(12) United States Patent
Ding et al.

(10) Patent No.: US 10,864,003 B2
(45) Date of Patent: Dec. 15, 2020

(54) ARTICULATION ASSEMBLIES FOR USE WITH ENDOSCOPIC SURGICAL INSTRUMENTS

(71) Applicant: COVIDIEN LP, Mansfield, MA (US)

(72) Inventors: Weijiang Ding, Shanghai (CN); Mingfeng Xu, Hefei (CN)

(73) Assignee: Covidien LP, Mansfield, MA (US)

( * ) Notice: Subject to any disclaimer, the term of this patent is extended or adjusted under 35 U.S.C. 154(b) by 295 days.

(21) Appl. No.: 15/765,518

(22) PCT Filed: Feb. 5, 2016

(86) PCT No.: PCT/CN2016/073584
§ 371 (c)(1),
(2) Date: Apr. 3, 2018

(87) PCT Pub. No.: WO2017/132970
PCT Pub. Date: Aug. 10, 2017

(65) Prior Publication Data
US 2020/0163687 A1    May 28, 2020

(51) Int. Cl.
*A61B 17/29* (2006.01)
*A61B 17/00* (2006.01)

(52) U.S. Cl.
CPC .... *A61B 17/29* (2013.01); *A61B 2017/00323* (2013.01); *A61B 2017/2908* (2013.01)

(58) Field of Classification Search
CPC ..... A61B 17/29; A61B 17/003; A61B 17/068; A61B 17/10; A61B 17/128; A61B 17/32;
(Continued)

(56) References Cited

U.S. PATENT DOCUMENTS

D249,549 S    9/1978  Pike
D263,020 S    2/1982  Rau, III
(Continued)

FOREIGN PATENT DOCUMENTS

CN    201299462 Y    9/2009
DE    2415263 A1    10/1975
(Continued)

OTHER PUBLICATIONS

Heniford et al. "Initial Research and Clinical Results with an Electrothermal Bipolar Vessel Sealer" Oct. 1999.
(Continued)

*Primary Examiner* — Melanie R Tyson
(74) *Attorney, Agent, or Firm* — Carter, DeLuca & Farrell LLP

(57) ABSTRACT

An articulation assembly (200) for use with a surgical instrument (100) is provided. The articulation assembly (200) includes a plurality of joints (260), a plurality of cables (240), and a first drive member (220). Each joint (260) defines a plurality of openings (262) extending longitudinally therethrough, a central opening (263) extending longitudinally therethrough, a pair of projections (268) extending from a first surface, and a pair of grooves (266) extending at least partially through a second surface. Each groove (266) of at least one joint (260) is configured to engage one projection (268) of the pair of projections (268) from an adjacent joint (260). Each cable (240) extends through one opening (262) of the plurality of openings (262) of each joint (260). The first drive member (220) extends through the central opening (263) of each joint (260).

13 Claims, 21 Drawing Sheets

(58) Field of Classification Search
CPC ............ A61B 17/3201; A61B 17/0467; A61B 17/0469; A61B 2017/2901; A61B 2017/2905; A61B 2017/2908; A61B 2017/00314; A61B 2017/00323
See application file for complete search history.

(56) References Cited

U.S. PATENT DOCUMENTS

| | | |
|---|---|---|
| D295,893 S | 5/1988 | Sharkany et al. |
| D295,894 S | 5/1988 | Sharkany et al. |
| D298,353 S | 11/1988 | Manno |
| D299,413 S | 1/1989 | DeCarolis |
| D343,453 S | 1/1994 | Noda |
| D348,930 S | 7/1994 | Olson |
| D349,341 S | 8/1994 | Lichtman et al. |
| D354,564 S | 1/1995 | Medema |
| D358,887 S | 5/1995 | Feinberg |
| D384,413 S | 9/1997 | Zlock et al. |
| H1745 H | 8/1998 | Paraschac |
| D402,028 S | 12/1998 | Grimm et al. |
| D408,018 S | 4/1999 | McNaughton |
| D416,089 S | 11/1999 | Barton et al. |
| D424,694 S | 5/2000 | Tetzlaff et al. |
| D425,201 S | 5/2000 | Tetzlaff et al. |
| H1904 H | 10/2000 | Yates et al. |
| D449,886 S | 10/2001 | Tetzlaff et al. |
| D453,923 S | 2/2002 | Olson |
| D454,951 S | 3/2002 | Bon |
| D457,958 S | 5/2002 | Dycus et al. |
| D457,959 S | 5/2002 | Tetzlaff et al. |
| H2037 H | 7/2002 | Yates et al. |
| D465,281 S | 11/2002 | Lang |
| D466,209 S | 11/2002 | Bon |
| D493,888 S | 8/2004 | Reschke |
| D496,997 S | 10/2004 | Dycus et al. |
| D499,181 S | 11/2004 | Dycus et al. |
| D502,994 S | 3/2005 | Blake, III |
| D509,297 S | 9/2005 | Wells |
| D525,361 S | 7/2006 | Hushka |
| D531,311 S | 10/2006 | Guerra et al. |
| D533,274 S | 12/2006 | Visconti et al. |
| D533,942 S | 12/2006 | Kerr et al. |
| D535,027 S | 1/2007 | James et al. |
| D538,932 S | 3/2007 | Malik |
| D541,418 S | 4/2007 | Schechter et al. |
| D541,611 S | 5/2007 | Aglassinger |
| D541,938 S | 5/2007 | Kerr et al. |
| D545,432 S | 6/2007 | Watanabe |
| D547,154 S | 7/2007 | Lee |
| D564,662 S | 3/2008 | Moses et al. |
| D567,943 S | 4/2008 | Moses et al. |
| D575,395 S | 8/2008 | Hushka |
| D575,401 S | 8/2008 | Hixson et al. |
| D582,038 S | 12/2008 | Swoyer et al. |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| D621,503 S | 8/2010 | Otten et al. |
| D627,462 S | 11/2010 | Kingsley |
| D628,289 S | 11/2010 | Romero |
| D628,290 S | 11/2010 | Romero |
| D630,324 S | 1/2011 | Reschke |
| D649,249 S | 11/2011 | Guerra |
| D649,643 S | 11/2011 | Allen, IV et al. |
| D661,394 S | 6/2012 | Romero et al. |
| D670,808 S | 11/2012 | Moua et al. |
| D680,220 S | 4/2013 | Rachlin |
| 9,084,608 B2 | 7/2015 | Larson et al. |
| 9,211,657 B2 | 12/2015 | Ackley et al. |
| 2011/0184459 A1* | 7/2011 | Malkowski ........ A61B 17/2909 606/206 |
| 2014/0221995 A1 | 8/2014 | Guerra et al. |
| 2014/0221999 A1 | 8/2014 | Cunningham et al. |
| 2014/0228842 A1 | 8/2014 | Dycus et al. |
| 2014/0230243 A1 | 8/2014 | Roy et al. |
| 2014/0236149 A1 | 8/2014 | Kharin et al. |
| 2014/0243811 A1 | 8/2014 | Reschke et al. |
| 2014/0243824 A1 | 8/2014 | Gilbert |
| 2014/0249528 A1 | 9/2014 | Hixson et al. |
| 2014/0250686 A1 | 9/2014 | Hempstead et al. |
| 2014/0257274 A1 | 9/2014 | McCullough, Jr. et al. |
| 2014/0257283 A1 | 9/2014 | Johnson et al. |
| 2014/0257284 A1 | 9/2014 | Artale |
| 2014/0257285 A1 | 9/2014 | Moua |
| 2014/0276803 A1 | 9/2014 | Hart |
| 2014/0284313 A1 | 9/2014 | Allen, IV et al. |
| 2014/0288549 A1 | 9/2014 | McKenna et al. |
| 2014/0288553 A1 | 9/2014 | Johnson et al. |
| 2014/0330308 A1 | 11/2014 | Hart et al. |
| 2014/0336635 A1 | 11/2014 | Hart et al. |
| 2014/0353188 A1 | 12/2014 | Reschke et al. |
| 2015/0018816 A1 | 1/2015 | Latimer |
| 2015/0025528 A1 | 1/2015 | Arts |
| 2015/0032106 A1 | 1/2015 | Rachlin |
| 2015/0051598 A1 | 2/2015 | Orszulak et al. |
| 2015/0051640 A1 | 2/2015 | Twomey et al. |
| 2015/0066026 A1 | 3/2015 | Hart et al. |
| 2015/0080880 A1 | 3/2015 | Sartor et al. |
| 2015/0080889 A1 | 3/2015 | Cunningham et al. |
| 2015/0082928 A1 | 3/2015 | Kappus et al. |
| 2015/0088122 A1 | 3/2015 | Jensen |
| 2015/0088126 A1 | 3/2015 | Duffin et al. |
| 2015/0088128 A1 | 3/2015 | Couture |
| 2015/0094714 A1 | 4/2015 | Lee et al. |

FOREIGN PATENT DOCUMENTS

| | | |
|---|---|---|
| DE | 02514501 A1 | 10/1976 |
| DE | 2627679 A1 | 1/1977 |
| DE | 03423356 C2 | 6/1986 |
| DE | 03612646 A1 | 4/1987 |
| DE | 3627221 A1 | 2/1988 |
| DE | 8712328 U1 | 2/1988 |
| DE | 04303882 C2 | 2/1995 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19751108 A1 | 5/1999 |
| DE | 19946527 C1 | 7/2001 |
| DE | 20121161 U1 | 4/2002 |
| DE | 10045375 C2 | 10/2002 |
| DE | 202007009165 U1 | 8/2007 |
| DE | 202007009317 U1 | 8/2007 |
| DE | 202007009318 U1 | 8/2007 |
| DE | 10031773 B4 | 11/2007 |
| DE | 202007016233 U1 | 1/2008 |
| DE | 19738457 B4 | 1/2009 |
| DE | 102004026179 B4 | 1/2009 |
| DE | 102008018406 B3 | 7/2009 |
| EP | 1281878 A1 | 2/2003 |
| EP | 1159926 A2 | 3/2003 |
| JP | 61501068 | 9/1984 |
| JP | 1024051 A | 1/1989 |
| JP | 1147150 A | 6/1989 |
| JP | 6502328 | 3/1992 |
| JP | 55106 | 1/1993 |
| JP | 0540112 | 2/1993 |
| JP | 0006030945 A | 2/1994 |
| JP | 6121797 A | 5/1994 |
| JP | 6285078 A | 10/1994 |
| JP | 06343644 A | 12/1994 |
| JP | 6511401 | 12/1994 |
| JP | 07265328 A | 10/1995 |
| JP | 856955 | 5/1996 |
| JP | 08252263 A | 10/1996 |
| JP | 8289895 A | 11/1996 |
| JP | 8317934 A | 12/1996 |
| JP | 8317936 A | 12/1996 |
| JP | 910223 C | 1/1997 |

(56) References Cited

FOREIGN PATENT DOCUMENTS

| | | | |
|---|---|---|---|
| JP | 09000538 | A | 1/1997 |
| JP | 9122138 | A | 5/1997 |
| JP | 0010000195 | A | 1/1998 |
| JP | 10155798 | A | 6/1998 |
| JP | 1147149 | | 2/1999 |
| JP | 11070124 | A | 3/1999 |
| JP | 11169381 | A | 6/1999 |
| JP | 11192238 | A | 7/1999 |
| JP | 11244298 | A | 9/1999 |
| JP | 2000102545 | A | 4/2000 |
| JP | 2000135222 | A | 5/2000 |
| JP | 2000342599 | A | 12/2000 |
| JP | 2000350732 | A | 12/2000 |
| JP | 2001008944 | A | 1/2001 |
| JP | 2001029355 | | 2/2001 |
| JP | 2001029356 | A | 2/2001 |
| JP | 2001003400 | | 4/2001 |
| JP | 2001128990 | A | 5/2001 |
| JP | 2001190564 | A | 7/2001 |
| JP | 2002136525 | A | 5/2002 |
| JP | 2002528166 | A | 9/2002 |
| JP | 2003116871 | A | 4/2003 |
| JP | 2003175052 | A | 6/2003 |
| JP | 2003245285 | A | 9/2003 |
| JP | 2004517668 | A | 6/2004 |
| JP | 2004528869 | A | 9/2004 |
| JP | 2005152663 | A | 6/2005 |
| JP | 2005253789 | A | 9/2005 |
| JP | 2005312807 | A | 11/2005 |
| JP | 2006015078 | A | 1/2006 |
| JP | 2006501939 | A | 1/2006 |
| JP | 2006095316 | A | 4/2006 |
| JP | 2008054926 | A | 3/2008 |
| JP | 2011125195 | A | 6/2011 |
| SU | 401367 | A1 | 11/1974 |
| WO | 0036986 | A1 | 6/2000 |
| WO | 0059392 | A1 | 10/2000 |
| WO | 0115614 | A1 | 3/2001 |
| WO | 0154604 | A1 | 8/2001 |
| WO | 0245589 | | 6/2002 |
| WO | 2006021269 | A1 | 3/2006 |
| WO | 2005110264 | A2 | 4/2006 |
| WO | 2008040483 | A1 | 4/2008 |
| WO | 2011018154 | A1 | 2/2011 |

OTHER PUBLICATIONS

Michael Choti, "Abdominoperineal Resection with the LigaSure Vessel Sealing System and LigaSure Atlas 20 cm Open Instrument"; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps", Feb. 6, 1967 (Feb. 6, 1967), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center,Charlotte,NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000. (6 pages).
Johnson et al. "Evaluation of a Bipolar Electrothermal Vessel Sealing Device in Hemorrhoidectomy" Sales/Product Literature; Jan. 2004. (1 page).
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12:876-878.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Results with an Electrothermal Bipolar Vessel Sealer" Surgical Endoscopy (2000) 15:799-801. (4 pages).
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001. (1 page).
Bergdahl et al. "Studies on Coagulation and the Development of an Automatic Computerized Bipolar Coagulator" J. Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003. (15 pages).
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.

(56) References Cited

OTHER PUBLICATIONS

Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C . . . (1 page).
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
U.S. Appl. No. 08/926,869, filed Sep. 10, 1997; inventor: James G. Chandler, Abandoned.
U.S. Appl. No. 09/177,950, filed Oct. 23, 1998; inventor: Randel A. Frazier, abandoned.
U.S. Appl. No. 09/387,883, filed Sep. 1, 1999; inventor: Dale F. Schmaltz, abandoned.
U.S. Appl. No. 09/591,328, filed Jun. 9, 2000; inventor: Thomas P. Ryan, abandoned.
U.S. Appl. No. 12/336,970, filed Dec. 17, 2008; inventor: Paul R. Sremeich, abandoned.
U.S. Appl. No. 14/065,644, filed Oct. 29, 2013; inventor: Reschke, abandoned.

* cited by examiner

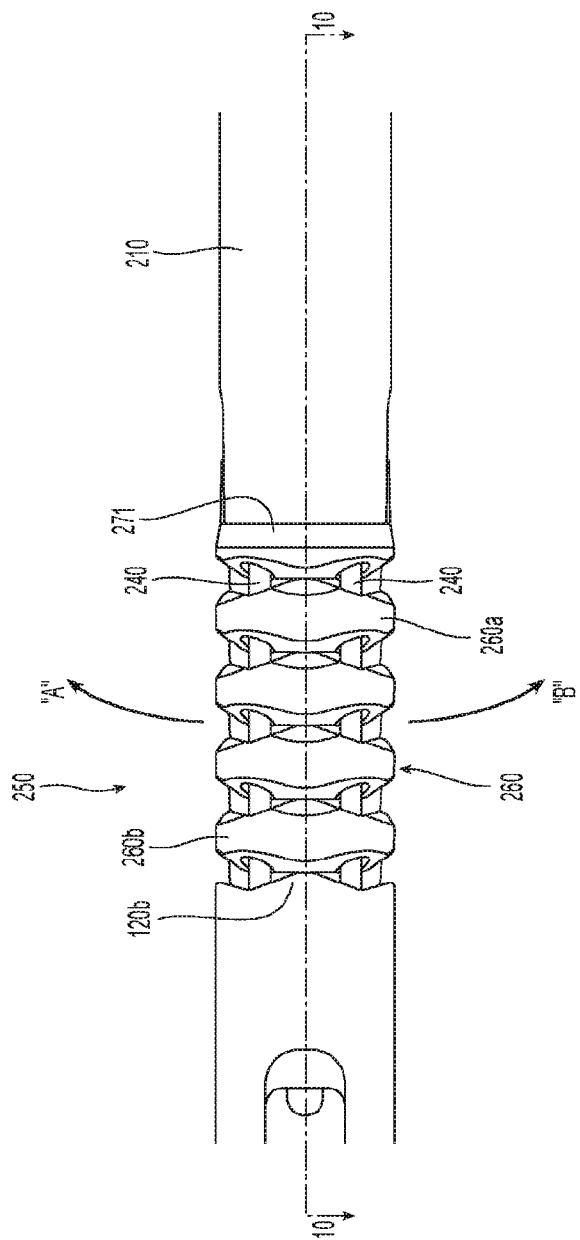

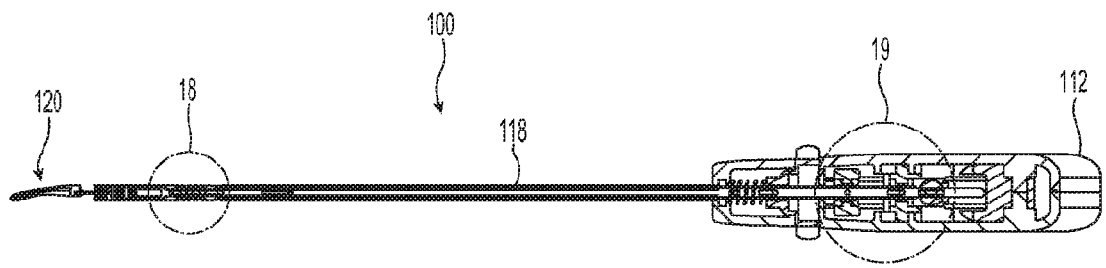
Fig. 17
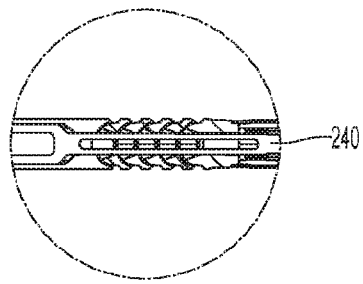 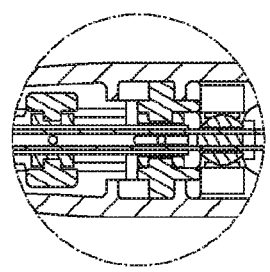
Fig. 18  Fig. 19
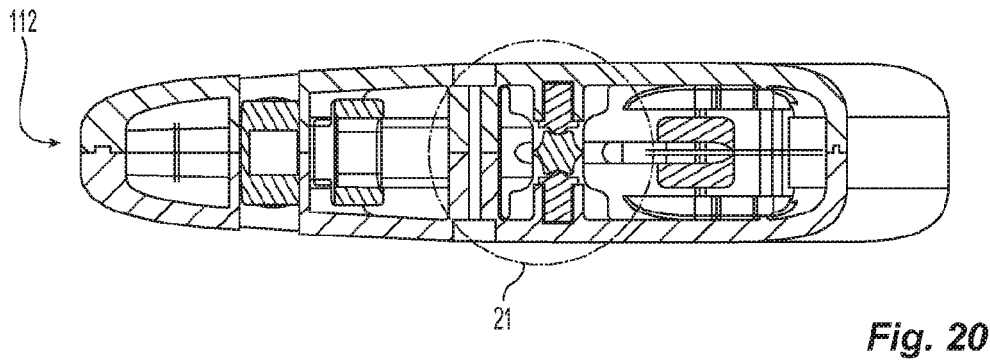
Fig. 20
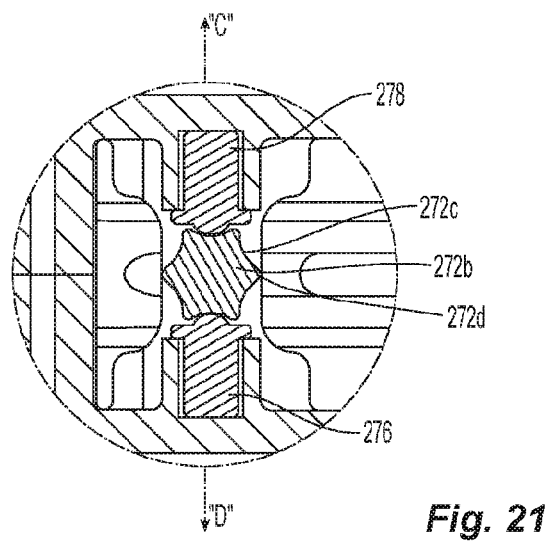
Fig. 21

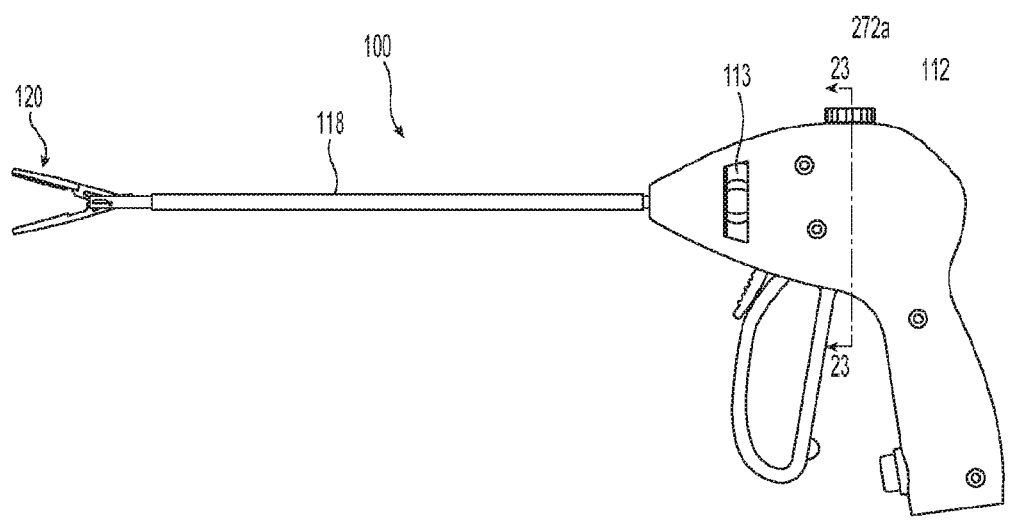
*Fig. 22*
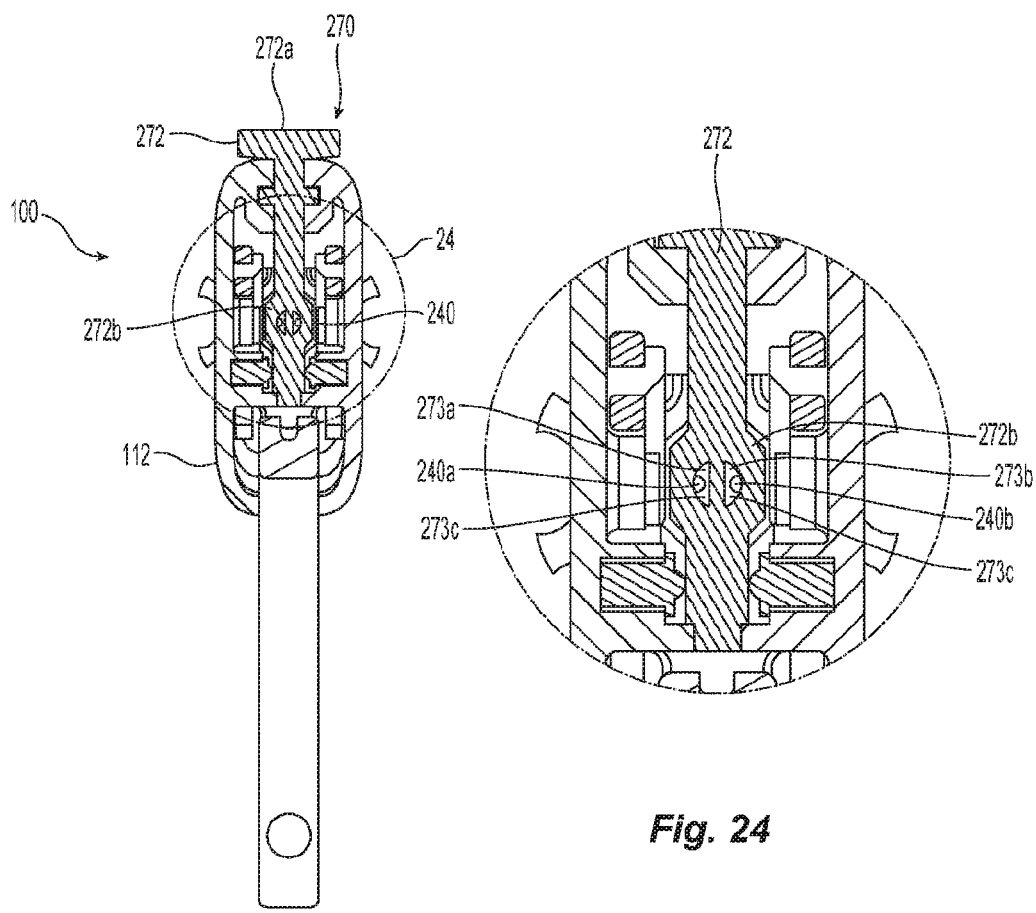
*Fig. 24*
*Fig. 23*

ARTICULATION ASSEMBLIES FOR USE WITH ENDOSCOPIC SURGICAL INSTRUMENTS

BACKGROUND

Technical Field

The present disclosure relates to articulation assemblies for use with surgical instruments and, more particularly, to articulation assemblies for use with surgical instruments including jaw members for grasping, treating, sealing, stapling, and/or dividing tissue.

Description of Related Art

Many surgical instruments are known for sealing, stapling, or otherwise joining tissue. Some of these surgical include one or more movable handles, levers, actuators, triggers, etc. for actuating and/or manipulating one or more functional components of the surgical instrument. For example, a surgical forceps may include a movable handle that is selectively actuatable relative to a stationary handle for moving at least one jaw member with respect to another jaw member of the forceps between spaced-apart and approximated positions for grasping tissue therebetween. Such a forceps may further include additional triggers for selectively actuating electrosurgical energy or for deploying staples, and/or for deploying a knife between the jaw members to cut tissue grasped therebetween.

In certain types of surgical procedures, it may be useful to use an energy-based device during endoscopic, laparoscopic and other minimally invasive surgeries.

During use in minimally invasive surgeries, one noted challenge for surgeons has been the inability to manipulate the jaw members or end effector assembly of the surgical forceps to grasp tissue in multiple planes, i.e., off-axis, while generating the required forces to affect a reliable seal. It would therefore be desirable to develop an endoscopic or endoluminal surgical forceps that includes an end effector assembly capable of being manipulated along multiple axes to enable the surgeon to grasp and seal vessels lying along different planes within a surgical cavity.

SUMMARY

The present disclosure relates to an articulation assembly for use with a surgical instrument. The articulation assembly includes a plurality of joints, a plurality of cables, and a first drive member. Each joint defines a plurality of openings extending longitudinally therethrough, a central opening extending longitudinally therethrough, a pair of projections extending from a first surface, and a pair of grooves extending at least partially through a second surface. Each groove of at least one joint is configured to engage one projection of the pair of projections from an adjacent joint. Each cable extends through one opening of the plurality of openings of each joint. The first drive member extends through the central opening of each joint.

In aspects of the present disclosure, each projection of at least one joint is configured to be at least partially positioned within one groove of the pair of grooves of an adjacent joint.

In other aspects, each projection of at least one includes an arcuate surface configured to contact an arcuate wall defining the groove of an adjacent joint.

In yet other aspects, each joint of the plurality of joints is substantially identical.

In still other aspects, each joint of the plurality of joints includes a pair of contours and a pair of platforms, each contour of the pair of contours of at least one joint is configured to engage one platform of the pair of platforms of an adjacent joint. Each contour of the pair of contours of at least one joint may be configured to pivot with respect to one platform of the pair of platforms of an adjacent joint. Each contour of the pair of contours of at least one joint may also be configured to pivot against a flat surface of one platform of the pair of platforms of an adjacent joint. Each projection of each joint may be 90° offset from each groove, and each contour of each joint may be 90° offset from each platform In aspects of the present disclosure, a second drive member extends through the central opening of each joint. Each of the first drive member and the second drive member may include a semi-circular cross-section at locations that are longitudinally aligned with each joint.

In other aspects, the articulation assembly further comprising an actuator disposed in mechanical cooperation with a handle assembly of the surgical instrument. The cable actuator includes at least one aperture. The plurality of cables extends through the at least one aperture of the actuator.

In yet other aspects, the plurality of cables includes four cables. The articulation assembly may further comprise an actuator disposed in mechanical cooperation with a handle assembly of the surgical instrument. The cable actuator includes a first aperture and a second aperture defined therethrough. Two cables of the plurality of cables extend through the first aperture of the actuator, and two cables of the plurality of cables extend through the second aperture of the actuator.

The present disclosure also relates to an articulation assembly for use with a surgical instrument. The articulation assembly includes a pivot, a drive member, and an outer tube. The pivot includes a first lateral pivot pin, a second lateral pivot pin, an upper pivot portion, a lower pivot portion, and an aperture extending therethrough. The first lateral pivot pin is disposed in mechanical cooperation with the first jaw member, the second lateral pivot pin is disposed in mechanical cooperation with the second jaw member. A portion of the drive member extends through the aperture of the pivot. The outer tube includes an upper aperture pivotally engaged with the upper pivot portion of the pivot, and a lower aperture pivotally engaged with the lower pivot portion of the pivot. The pivot is configured to pivot about a first axis defined therethrough to cause articulation of the jaw members, and the jaw members are configured to pivot about a second axis defined through the pivot to cause the jaw members to move between an open position and an approximated position.

In aspects of the present disclosure, a reduced-perimeter portion of the drive member is longitudinally aligned with the aperture of the pivot.

In other aspects, the articulation assembly further comprises a distal member disposed in mechanical cooperation with the pivot. The distal member is rotatable with respect to the drive member. The distal member may include a first angled slot defined therein and configured to engage the first lateral pivot pin and a second angled slot defined therein and configured to engage the second lateral pivot pin.

In yet other aspects, the articulation assembly comprises a control member disposed in mechanical cooperation with only one of the first lateral pivot pin or the second lateral pivot pin. The control member may include a T-shaped slot configured to engage a T-shaped portion of the pivot.

BRIEF DESCRIPTION OF THE DRAWINGS

Various aspects of the present disclosure are described herein with reference to the drawings wherein like reference numerals identify similar or identical elements:

FIG. 5 is an enlarged view of the portion of the first articulation assembly indicated in FIG. 3;

FIG. 6 is a side view of the portion of the first articulation assembly shown in FIG. 5;

FIG. 17 is a cross-sectional view of the surgical instrument of FIG. 14 taken along line 17-17;

FIGS. 18 and 19 are enlarged views of the areas of detail indicated in FIG. 17;

FIG. 20 is a cross-sectional view of the surgical instrument of FIG. 14 taken along line 20-20;

FIG. 21 is an enlarged view of the area of detail indicated in FIG. 20;

FIG. 22 is a side view of the surgical instrument of FIG. 1;

FIG. 23 is a cross-sectional view of the surgical instrument of FIG. 22 taken along line 23-23;

FIG. 24 is an enlarged view of the area of detail indicated in FIG. 23;

DETAILED DESCRIPTION

Figure 1:
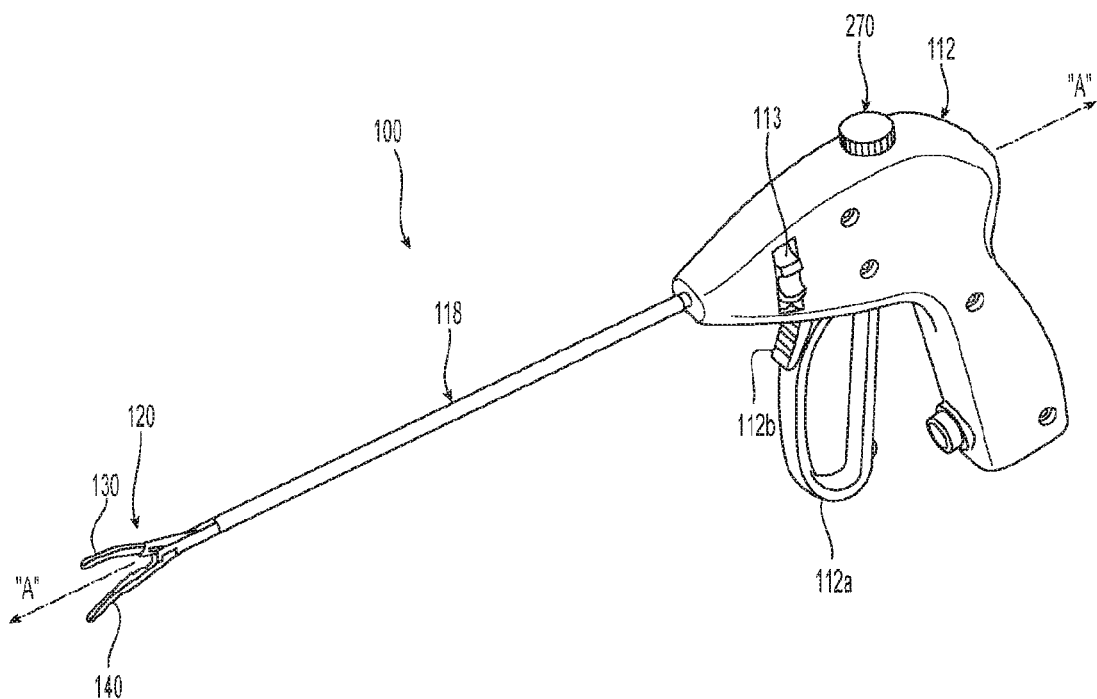
FIG. 1 is a perspective view of an embodiment of a surgical instrument in accordance with the present disclosure including a first articulation assembly.
Figure 2:
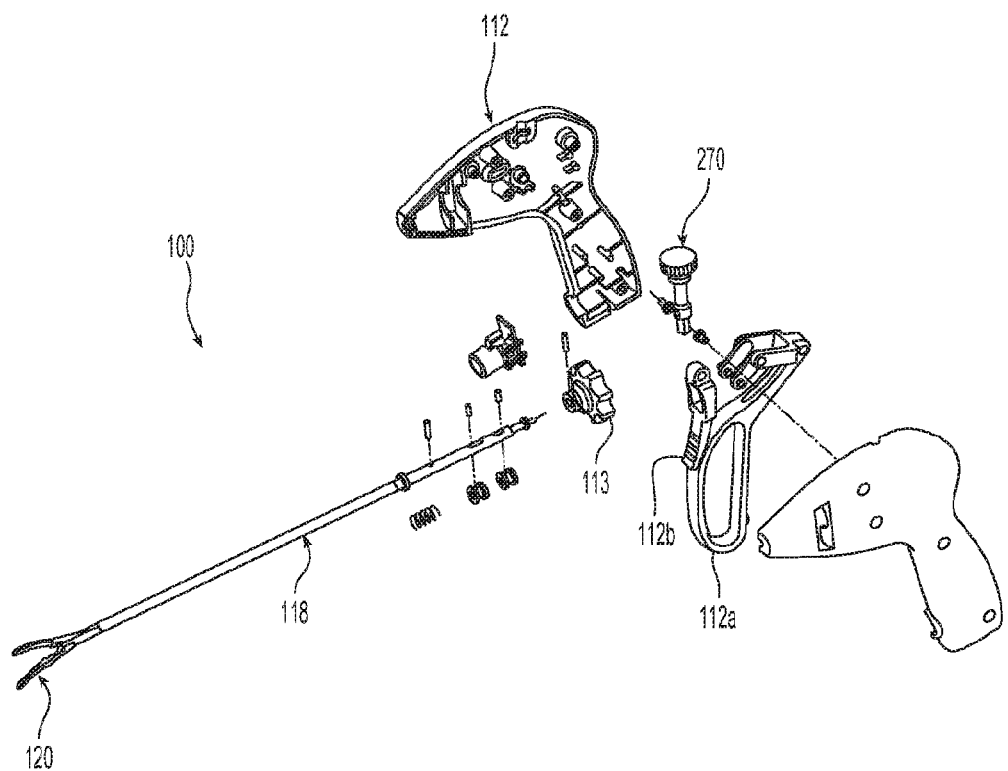
FIG. 2 is an assembly view of the surgical instrument of FIG. 1.
Figure 3:
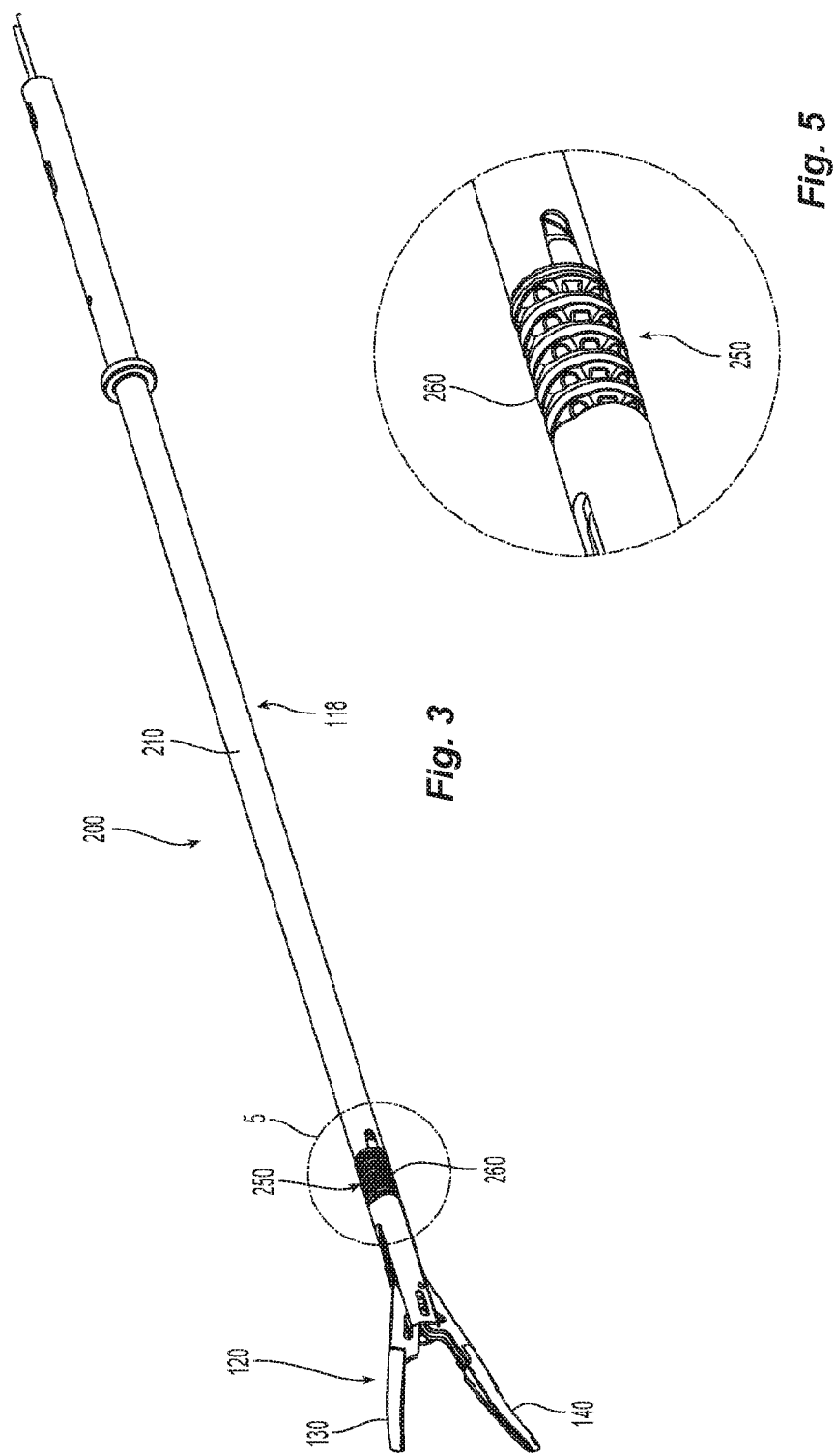
FIG. 3 is a perspective view of the first articulation assembly of the surgical instrument of FIGS. 1 and 2.

Embodiments of the presently disclosed surgical instrument are described in detail with reference to the drawings, in which like reference numerals designate identical or corresponding elements in each of the several views. As used herein the term "distal" refers to that portion of the surgical instrument that is farther from the user, while the term "proximal" refers to that portion of the surgical instrument that is closer to the user.

Referring initially to FIG. 1, an embodiment of a surgical instrument 100 is shown for use with various surgical procedures. Surgical instrument 100 may be configured to connect to a source of electrosurgical energy (not shown) via a connector assembly, and/or may contain an independent energy source e.g., a battery (not shown). The use of an electrosurgical apparatus to apply electrosurgical energy to tissue is generally described in U.S. Pat. No. 7,083,618, which is incorporated herein in its entirety by reference.

Surgical instrument 100 includes a housing or handle assembly 112 near a proximal end, an end effector 120 near a distal end and an elongated shaft 118 extending therebetween. A proximal portion of elongated shaft 118 defines a longitudinal axis "A-A." The end effector 120 includes a first jaw member 130 and a second jaw member 140, which are movable relative to each other. The end effector 120 may be positioned within a body cavity to engage tissue at a surgical site while handle assembly 112 is manipulatable by a surgeon from outside the body cavity to control the movement and operation of the end effector 120. Handle assembly 112 includes a movable handle 112a, which is manipulatable to open and close jaw members 130, 140 of the end effector 120, and a trigger 112b, which is manipulatable to initiate an electrosurgical current.

Actuation of the movable handle 112a longitudinally translates a drive bar or a control rod of a drive assembly to approximate jaw members 130, 140 and to apply a pressure between the jaw members 130 and 140 in the range of about 3 kg/cm$^2$ to about 16 kg/cm$^2$. Further details of a vessel sealing device including a handle assembly and drive assembly for controlling actuation of an end effector can be found in U.S. Pat. Nos. 7,101,371 and 7,083,618, which are incorporated herein in their entirety by reference.

In the approximated configuration where tissue can be grasped and/or cut between the jaw members 130, 140, a separation or gap distance is maintained between the jaw members 130, 140 by one or more stop members (not shown). In some embodiments, to provide an effective tissue seal, an appropriate gap distance of between about 0.001 inches to about 0.006 inches may be provided. The stop members may be positioned on one or more jaw members 130, 140 and may be made from a thermally sprayed ceramic (e.g. Alumina Titania), epoxy, or a high temperature plastic, for example. Other configurations are also contemplated.

The present disclosure includes elongated shaft 118 that is articulatable or movable off-axis to help increase the functionality of the surgical instrument 100. To achieve the articulation or off-axis movement of the elongated shaft 118, various articulation mechanisms are disclosed. In FIGS. 1-24, a first articulation mechanism 200 is shown; in FIGS. 25-42, a second articulation mechanism 300 is shown; and in FIGS. 43-47, a third articulation mechanism 400 is shown.

With initial reference to FIGS. 1-4, surgical instrument 100 includes first articulation mechanism 200 having an outer tube 210, a first drive member 220, a second drive member 230, a plurality of cables 240, and a joint assembly 250 including a plurality of joints 260. Generally, first drive member 220 and second drive member 230 are translatable to seal and cut tissue between the jaw members 130 and 140, as described in detail in the patents incorporated by reference hereinabove, and cables 240 are translatable to cause end effector 120 (and a distal portion of elongated shaft 118) to articulate with respect to the longitudinal axis "A-A." As discussed in further detail below, a cable actuator 270 disposed in mechanical cooperation with handle assembly 112 is configured to move cables 240 and thereby cause articulation of end effector 120.

Figure 7:
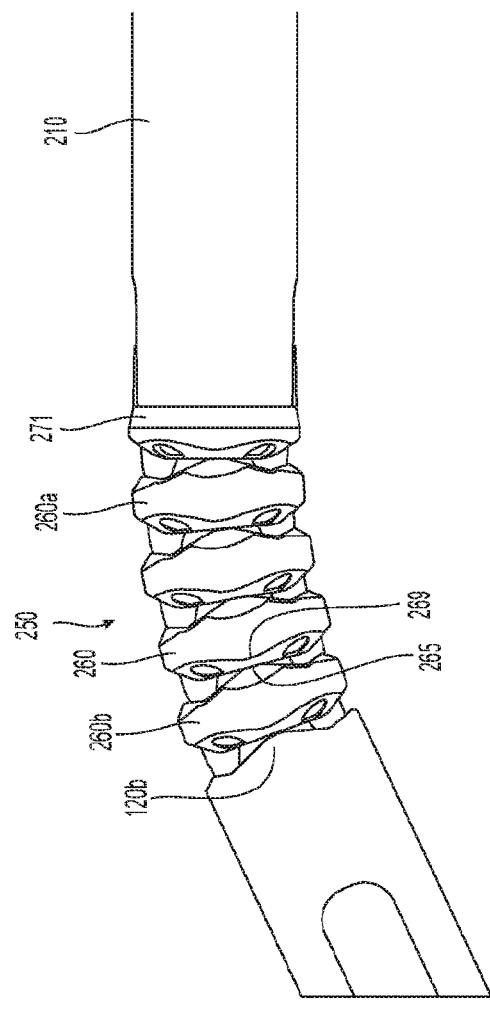
FIG. 7 is a side view of the portion of the first articulation assembly shown in FIGS. 5 and 6 illustrated in an articulation position.

With reference to FIGS. 6-13, joint assembly 250 and the plurality of joints 260 are shown. Movement of cables 240 causes joint assembly 250 to move between a first, generally linear configuration (FIGS. 6, 8 and 9-11) and a second, angled or articulated configuration (FIG. 7). Each joint 260 is configured to engage at least one directly adjacent joint 260, and is articulatable or pivotable with respect to the adjacent joint 260. A proximal-most joint 260a is also configured to engage a link joint 271 (FIGS. 6 and 7) disposed proximally adjacent thereto and is articulatable or pivotal with respect thereto. Link joint 271 is also configured to engage outer tube 210. A distal-most joint 260b is also configured to engage a proximal end 120b of end effector 120 and is articulatable or pivotal with respect thereto.

Figure 12:
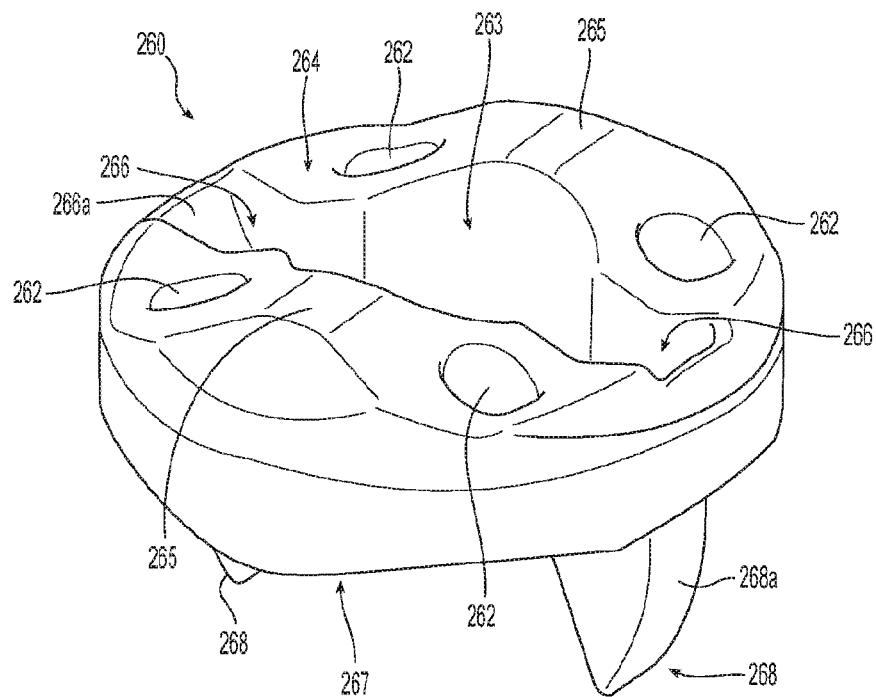
FIG. 12 is a perspective view of a joint of the first articulation assembly.
Figure 13:
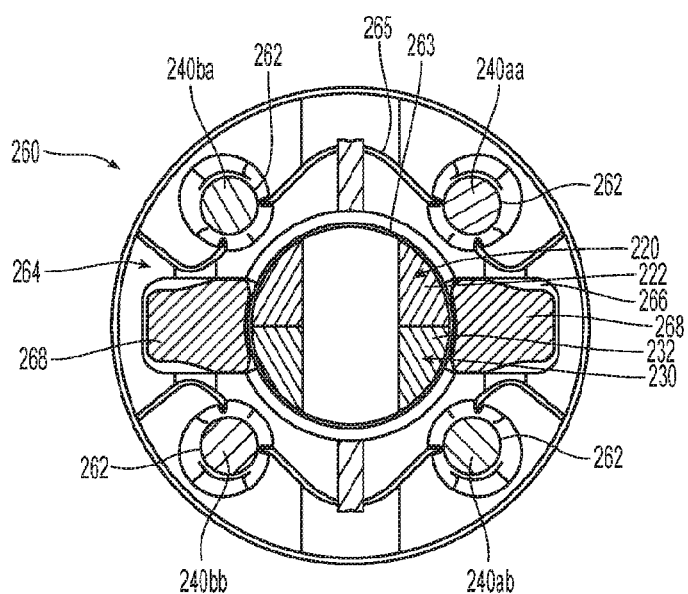
FIG. 13 is a cross-sectional view of a portion of the first articulation assembly of FIG. 9 taken along line 13-13.
Figure 14:
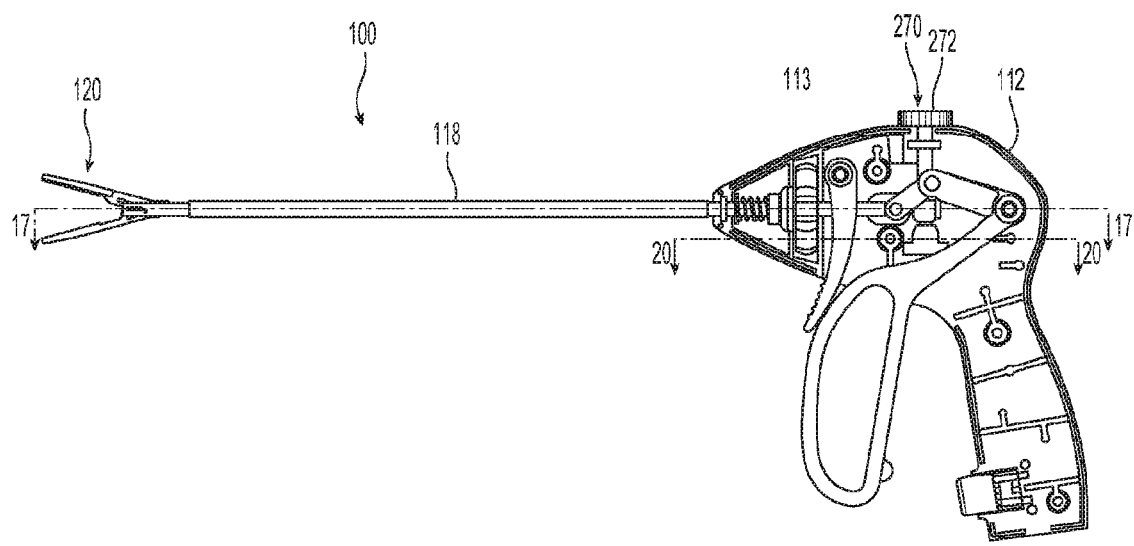
FIG. 14 is an internal view of the surgical instrument of FIG. 1.
Figure 15:
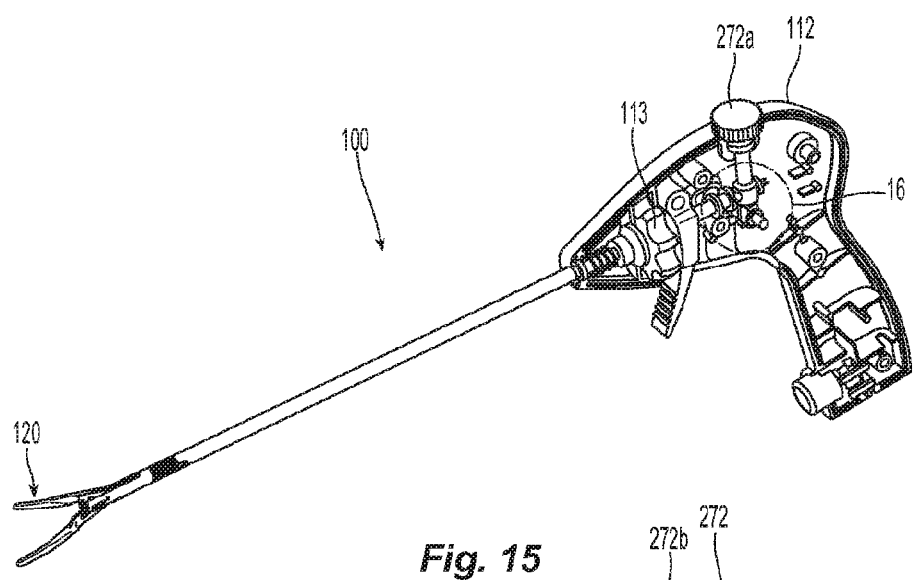
FIG. 15 is an internal view of the surgical instrument of FIGS. 1 and 14.

Referring now to FIG. 12, a single joint 260 is shown, and FIG. 13, a cross-section of a first joint 260 is shown engaged with a second joint 260. Joint 260 includes various features that enable joint 260 to articulate or pivot in a plurality of directions with respect to an adjacent joint 260 and/or with link joint 271 and proximal end 120b of end effector 120. In disclosed embodiments, each joint 260 is identical or substantially identical to all of the other joints 260.

Joint 260 includes a plurality of openings 262 extending longitudinally therethrough; each opening 262 is configured to allow one cable 240 or a portion one cable 240 to pass therethrough. A central opening 263 is also included on each joint 260 to allow first drive member 220 and second drive member 230 to pass therethrough (see FIG. 13). A proximal portion 264 of each joint 260 includes a pair of contours 265 and a pair of grooves 266 (e.g., including an arcuate surface), which extend through joint 260. A distal portion 267 of each joint 260 includes a pair of projections 268 extending therefrom, and a pair of platforms 269 (e.g., linear or flat surfaces; see FIG. 7) thereon. In FIG. 13, projections 268 from a second joint are shown within grooves 266 of a first joint.

Each contour 265 is configured to engage a single platform 269; contours 265 and platforms 269 are configured to pivot a predetermined amount with respect to each other in the general directions of arrows "A" and "B" in FIG. 6. Each projection 268 is configured to engage (e.g., be positioned at least partially within) a single groove 266. As shown in FIG. 12, projections 268 include an arcuate surface 268a, which engages a corresponding arcuate surface 266a of groove 266. The engagement between projections 268 and grooves 266 enables or facilitates the pivotal movement between adjacent joints 260, for example. Further, each projections 265/groove 266 is 90° offset from each contour 265/platform 269, thereby enabling the pivotal movement in the directions of arrows "A" and "B."

In the illustrated embodiments, joint assembly 250 includes four joints 260, however more or fewer joints 260 may be included without departing from the scope of the present disclosure. In embodiments where more than four joints 260 are included, the geometry of various features of the joints 260 can be altered to allow a relatively smaller amount of pivotal movement between adjacent joints 260. In embodiments where fewer than four joints 260 are included, the geometry of various features of the joints 260 can be altered to allow a relatively larger amount of pivotal movement between adjacent joints 260. In each of these situations, the total amount of desired articulation (e.g., up to about 45°) may be accomplished.

Figure 11:
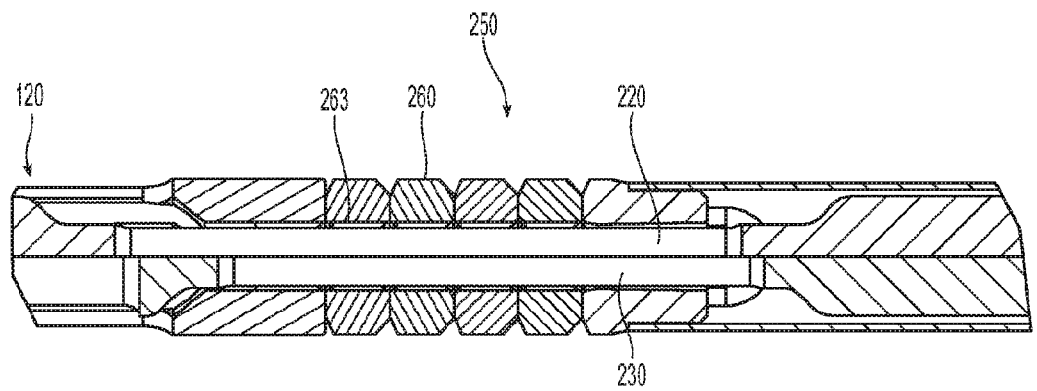
FIG. 11 is a cross-sectional view of a portion of the first articulation assembly of FIG. 9 taken along line 11-11.

With particular reference to FIGS. 11 and 13, cross-sectional views of a portion of surgical instrument 100 are shown and further illustrate details of the first drive member 220 and the second drive member 230. Each drive member 220, 230 extends from handle assembly 112, through central opening 263 of each joint 260, and into contact with end effector 120. At least in the locations where each drive member 220, 230 passes through central opening 263 of each joint 260, the drive members 220, 230 are hollow and/or only include sidewalls 222, 232, respectively (e.g., semi-circles) (see FIG. 13). Additionally, at these locations, the diameter of each drive member 220, 230 is reduced with respect to proximally-adjacent portions 224, 234 and distally-adjacent portions 225, 235, respectively (see FIG. 4). The cross-sectional shapes and the reduced-diameter sections help allow drive members 220, 230 to curve (upon articulation of joints 260) while still maintaining the strength desired to transfer force from handle assembly 112 to end effector 120.

Figure 8:
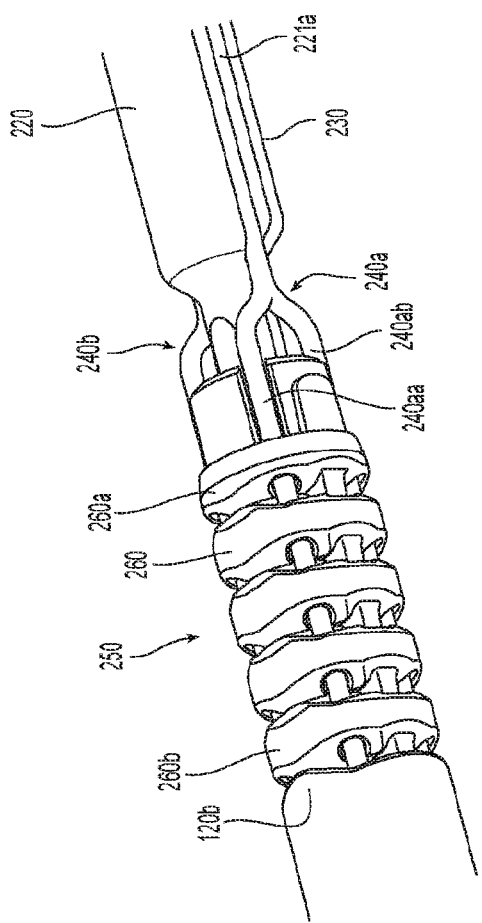
FIG. 8 is a perspective view of a portion of the first articulation assembly with some features omitted.
Figure 9:
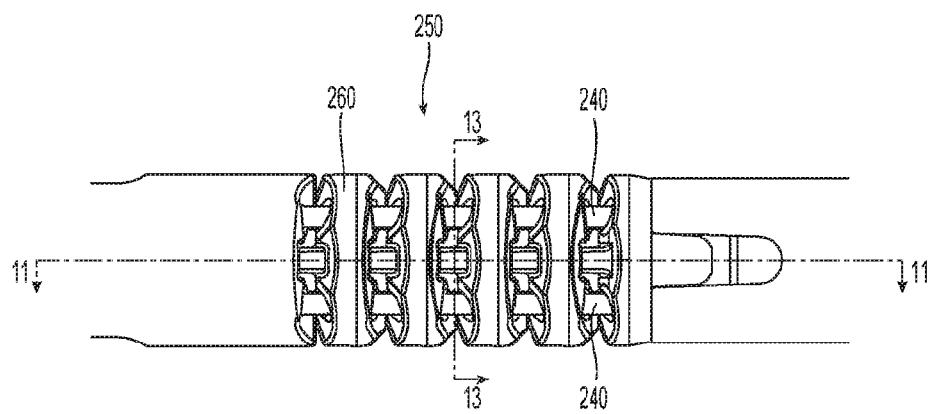
FIG. 9 is a side view of the portion of the first articulation assembly shown in FIG. 5.
Figure 10:
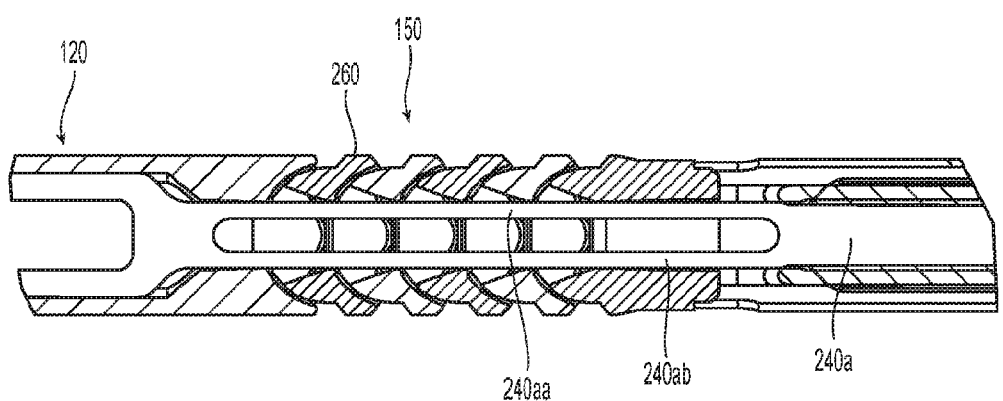
FIG. 10 is a cross-sectional view of a portion of the first articulation assembly of FIG. 6 taken along line 10-10.

Additionally, with particular reference to FIG. 8, first drive member 220 and second drive member 230 form a pair of slots (one slot 221a is shown in FIG. 8), with each slot (e.g., 221a) being configured to allow at least one cable 240 to pass therethrough.

Figure 4:
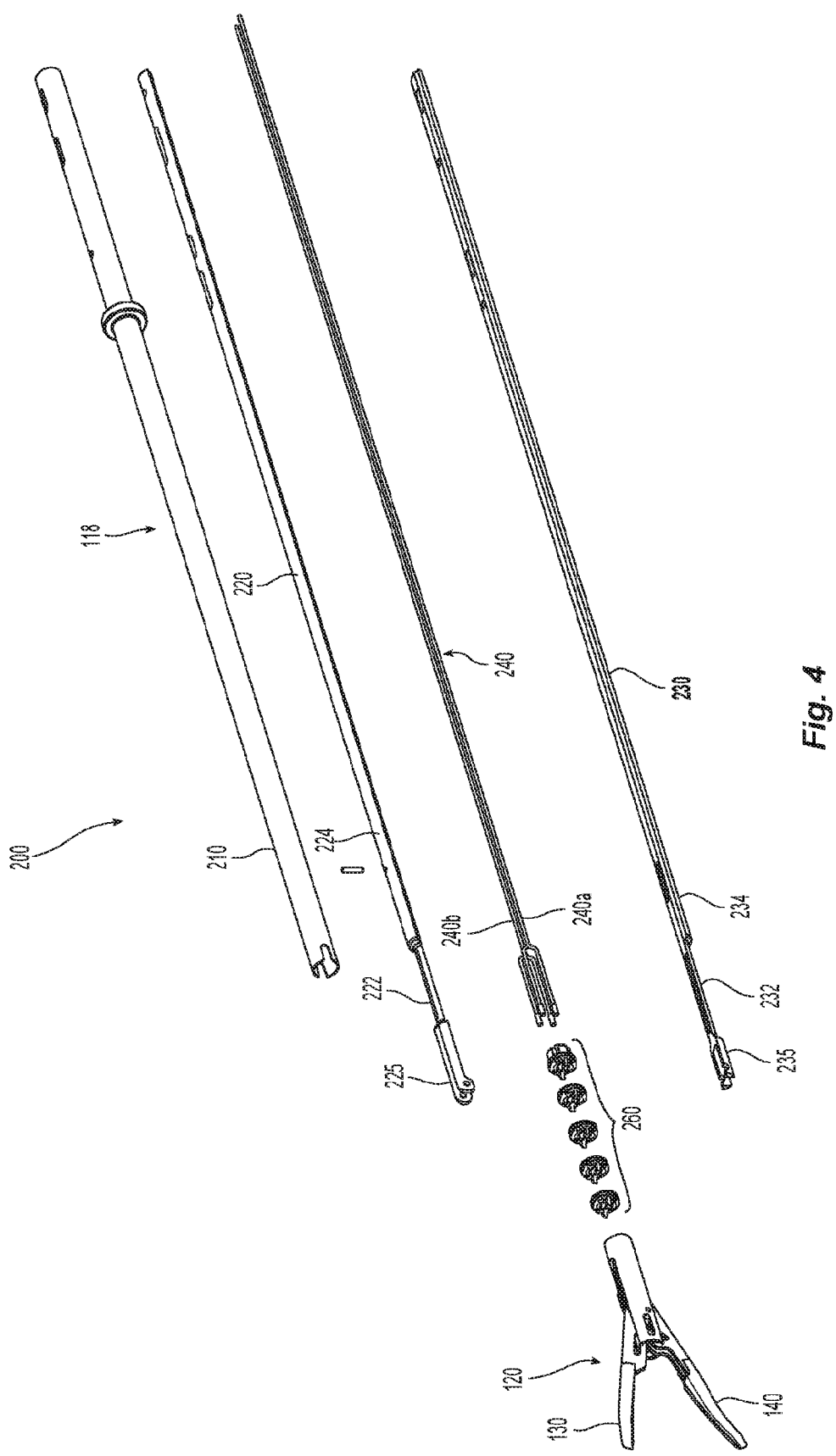
FIG. 4 is an assembly view of the first articulation assembly of FIG. 3.

Cables 240 extend between handle assembly 112, through openings 262 of joints 260, and into mechanical engagement with end effector 120. More particularly, cables 240 include a first cable 240a and a second cable 240b (see FIG. 8). First cable 240a is formed from two cables 240aa and 240ab (see FIGS. 8 and 13) twisted together or otherwise engaged, and second cable 240b is formed from two cables 240ba and 240bb (see FIG. 13) twisted together or otherwise combined. As shown in FIG. 4, a majority of the length of cables 240 includes the twisted or combined cables 240a, 240b; the portions of cables 240 that extend through openings 262 of joints 260 are single, untwisted cables 240aa, 240ab, 240ba, 240bb.

Figure 16:
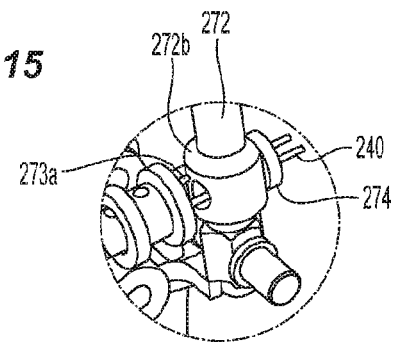
FIG. 16 is an enlarged view of the area of detail indicated in FIG. 15.

With particular reference to FIGS. 14-24, cable actuator 270 is disposed in mechanical cooperation with handle assembly 112 and is configured to move cables 240 and thereby cause articulation of end effector 120. Cable actuator includes a controller 272, a flange 274, a first plunger 276 and a second plunger 278. A first or upper portion 272a of controller 272 rests atop handle assembly 112 and is accessible to a user. A second portion 272b of controller 272 is disposed within handle assembly 112 and includes a first aperture 273a and a second aperture 273b (FIG. 24) extending longitudinally therethrough; cables 240 extend through apertures 273a, 273b of controller 272. As shown in FIG. 16, flange 274 is disposed proximally of second portion 272b of controller 272 and is configured to engage cables 240; cables 240 are shown extending through an opening of flange 274. Cables 240 are longitudinally fixed with respect to flange 274.

With particular reference to FIG. 21, the engagement between second portion 272b of controller 272 and plungers 276, 278 is shown. Second portion 272b of controller 272 includes a plurality of recesses 272c, with each adjacent recess 272c separated by a ridge 272d. Each plunger 276, 278 is configured to engage one recess 272c at a time. More particularly, each plunger 276 is biased into engagement with one recess 272c (e.g., by a biasing element).

As first portion 272a of controller 272 is rotated, each plunger 276, 278 is contacted by a respective ridge 272d, which forces plungers 276, 278 laterally outward in the general direction of arrows "C" and "D" in FIG. 21, such that plungers 276, 278 are out of contact with recesses 272c. Upon further rotation of first portion 272a of controller 272, plungers 276, 278 are urged into engagement with different (e.g., adjacent) recesses 272c. The engagement between plungers 276, 278 and recesses 272c releasably maintains controller 272 in its rotational position.

Further, and with particular reference to FIGS. 16 and 24, due at least in part to the engagement between cables 240 apertures 273a, 273b of controller 272, the rotation of controller 272 exerts a force on first cable 240a and second cable 240b. More particularly, rotation of controller 272 causes sidewalls 273c of apertures 273a, 273b to exert a proximal force against one cable (e.g., first cable 240a) and a distal force against one cable (e.g., second cable 240b). Additionally, as noted above, longitudinal translation of cables 240 causes articulation of end effector 120.

Accordingly, rotation of controller 272 in a first direction (e.g., clockwise) causes first cable 240a to be pushed distally, causes second cable 240b to be pulled proximally, which causes joint assembly 250 and thus end effector 120 to articulate in the general direction of arrow "B" (FIG. 6). Rotation of controller 272 in a second direction (e.g., counter-clockwise) causes first cable 240a to be pulled proximally, causes second cable 240b to be pushed distally, which causes joint assembly 250 and thus end effector 120 to articulate in the general direction of arrow "A" (FIG. 6). Further, the particular amount and spacing of recesses 272c and ridges 272d results in particular angles of articulation in which end effector 120 can be releasably maintained. Controllers 272 having recesses 272c and ridges 272d with different spacing from what is shown are encompassed by the present disclosure.

As shown in FIGS. 1, 2, 14, 15 and 22, handle assembly 112 also includes a knob 113. As discussed in detail in disclosures incorporated by reference, rotation of knob 113 results in rotation of elongated shaft 118, and thus end effector 120, about longitudinal axis "A-A." Here, outer tube 210, which at least partially radially surrounds first drive member 220 and second drive member 230, is engaged with knob 113. Accordingly, the combination of first articulation mechanism 200 and knob 113 enables a great amount of versatility regarding off-axis positioning of end effector 120.

Figure 25:
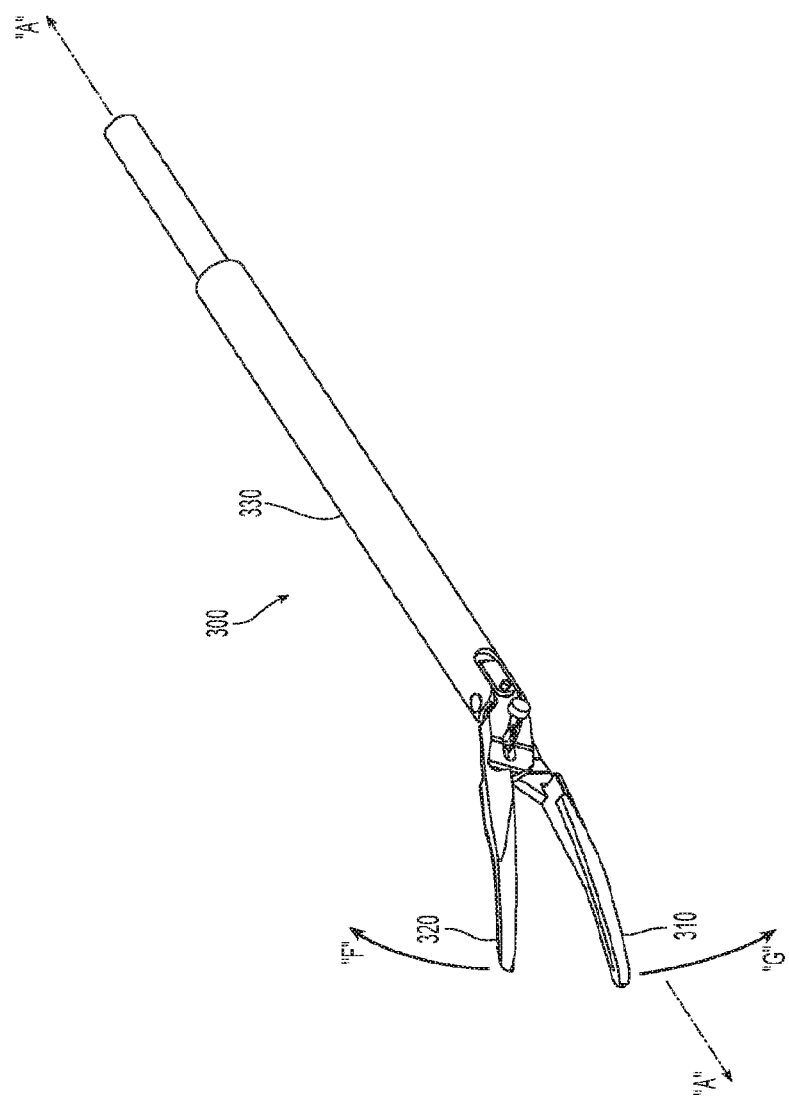
FIG. 25 is a perspective view of a second articulation assembly according to an embodiment of the present disclosure.
Figure 26:
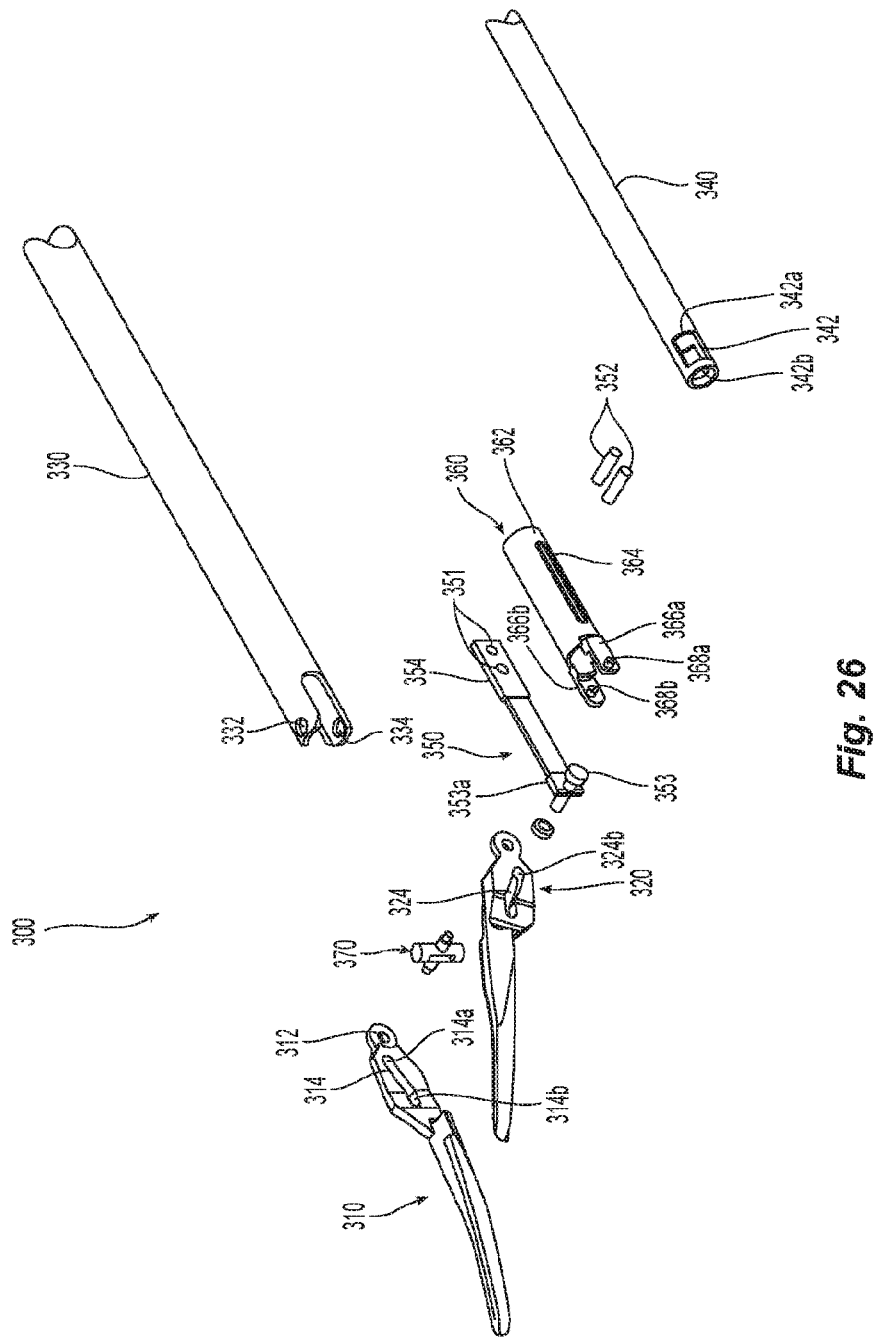
FIG. 26 is an assembly view of the second articulation assembly of FIG. 25.

Referring now to FIGS. 25-42, second articulation mechanism 300 is shown. With particular reference to FIGS. 25 and 26, second articulation mechanism 300 includes a first jaw 310, a second jaw 320, an outer tube 330, an inner tube 340, a drive member 350, a distal member 360, and a pivot 370. Generally, inner tube 340 and drive member 350 are translatable to seal and cut tissue held between first jaw 310 and second jaw 320, as described below and as described in patents incorporated herein. Distal member 360 is rotatable to cause first jaw member 310 and second jaw member 320 to articulate with respect to the longitudinal axis "A-A."

Initially, to seal tissue, a user causes inner tube 340 to be distally translated (e.g., by actuating a lever, knob or button on handle assembly). Inner tube 340 is connected to drive member 350 via pins 352, such that longitudinal translation of inner tube 340 causes a corresponding longitudinal translation of drive member 350. More particularly, a pair of pins 352 extends between a slot 342 defined adjacent a distal portion of inner tube 340, and a pair of holes 351 defined adjacent a proximal portion of drive member 350. Proximal and distal walls 342a, 342b of slot 340 limit the movement of pins 352 with respect to inner tube 340.

Figure 35:
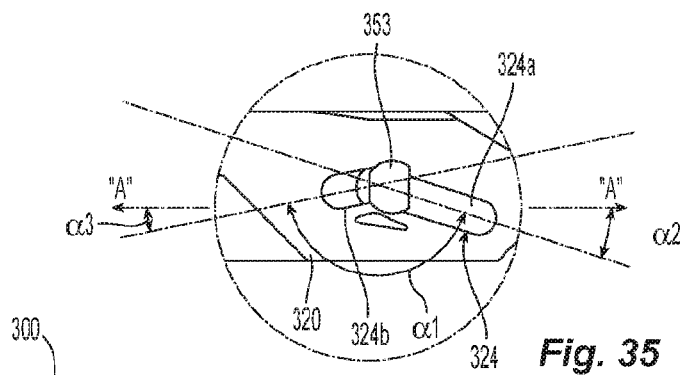
FIG. 35 is an enlarged view of the area of detail indicated in FIG. 34.
Figure 36:
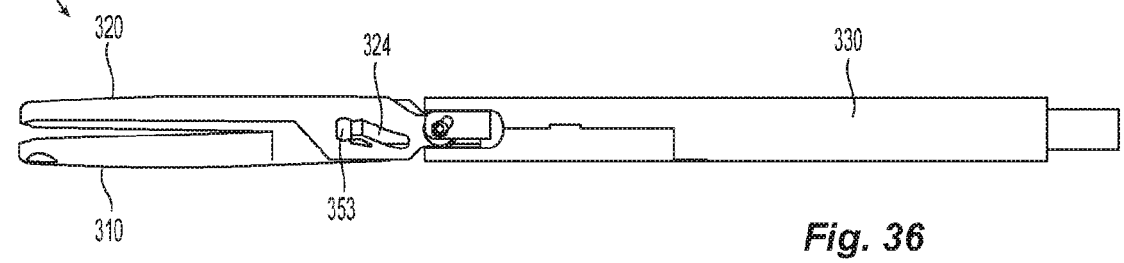
FIGS. 36 and 37 are side and top views, respectively, of the second articulation assembly of FIGS. 25 and 26 showing the jaw members in an approximated position and with various portions omitted.
Figure 37:
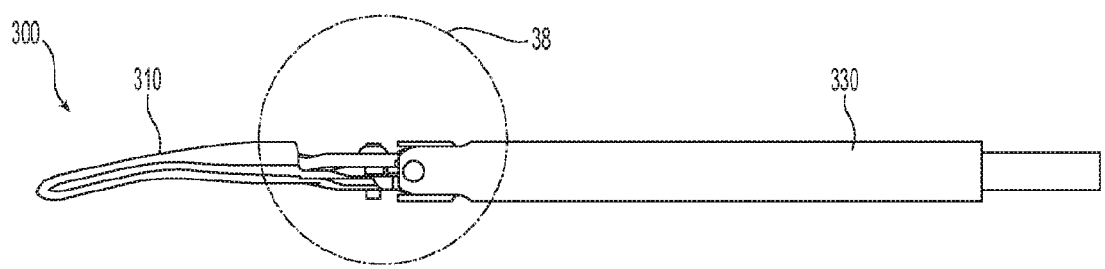
Figure 38:
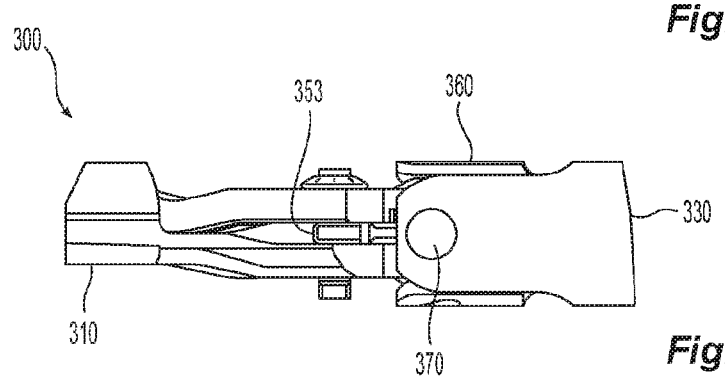
FIG. 38 is an enlarged view of the area of detail indicated in FIG. 37.
Figure 39:
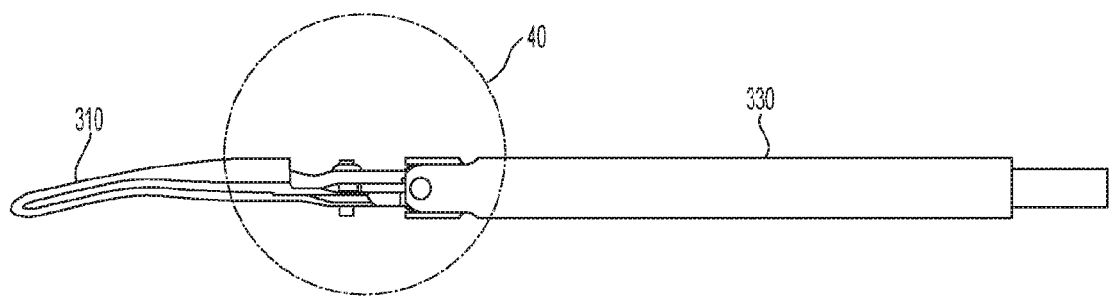
FIG. 39 is a top view of the second articulation assembly of FIGS. 25 and 26 showing the jaw members in an approximated position and with various portions omitted.
Figure 40:
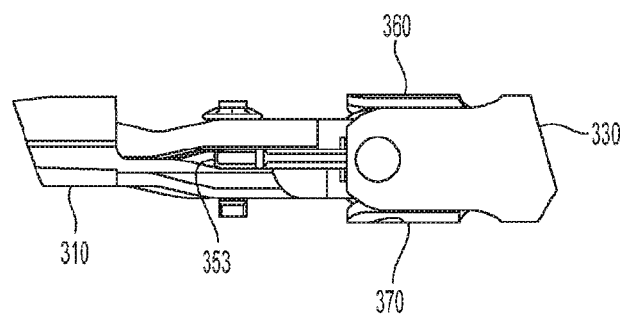
FIG. 40 is an enlarged view of the area of detail indicated in FIG. 39.
Figure 41:
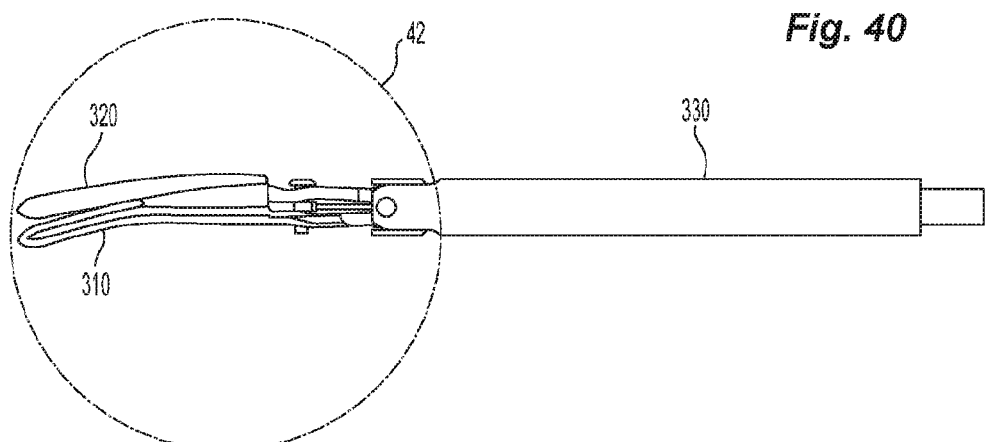
FIG. 41 is a top view of the second articulation assembly of FIGS. 25 and 26 showing the jaw members in an approximated position and with various portions omitted.
Figure 42:
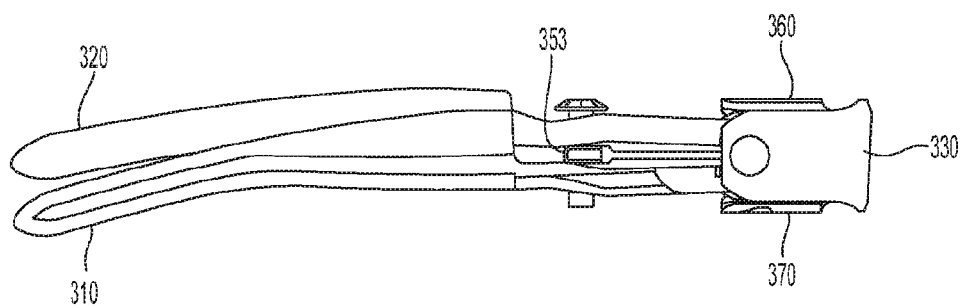
FIG. 42 is an enlarged view of the area of detail indicated in FIG. 41.

A drive pin 353 extends through a hole 353a in a distal portion of drive member 350, and extends through a slot 314 defined in first jaw 310 and a slot 324 defined in second jaw 320. Longitudinal translation of drive member 350 causes drive pin 353 to travel through slots 314, 324. More particularly, and with reference to FIGS. 26 and 35, each slot 314, 324 includes a first section 314a, 324a, respectively, and a second section 314b, 324b, respectively. First section 314a of slot 314 is generally linear and is disposed at a first angle (not explicitly shown in FIG. 35) (e.g., between about 110° and about 170°) with respect to second section 314b of slot 314, which is also generally linear. Likewise, and as illustrated in FIG. 35, first section 324a of slot 324 is generally linear and is disposed at a first angle α1 (e.g., between about 110° and about 170°) with respect to second section 324b of slot 324, which is also generally linear.

During the process of sealing tissue, drive pin 353 is within first sections 314a, 324a of slots 314, 324, respectively. When the jaw members 310, 320 are in the approximated position an angle α2 between first sections 314a, 324a with respect to longitudinal axis "A-A" is between about 20° and about 45° (see FIG. 35).

During the process of cutting tissue, after drive pin 353 has been distally advanced through first sections 314a, 324a, drive pin 353 is within second sections 314b, 324b of slots 314, 324, respectively. As shown in FIG. 35, when the jaw members 310, 320 are in the approximated position, an angle α3 between second sections 314b, 324b with respect to longitudinal axis "A-A" is between about 5° and about 15°.

With general regard to the pivotal movement of the jaw members, first jaw 310 and second jaw 320 are pivotable about a first pivot axis "P1" (FIG. 27) between an open position and an approximated position, and are pivotable about a second pivot axis "P2" (FIG. 27) in the general directions of arrows "F" and "G" in FIG. 25, which provides a varying degree of articulation.

Figure 27:
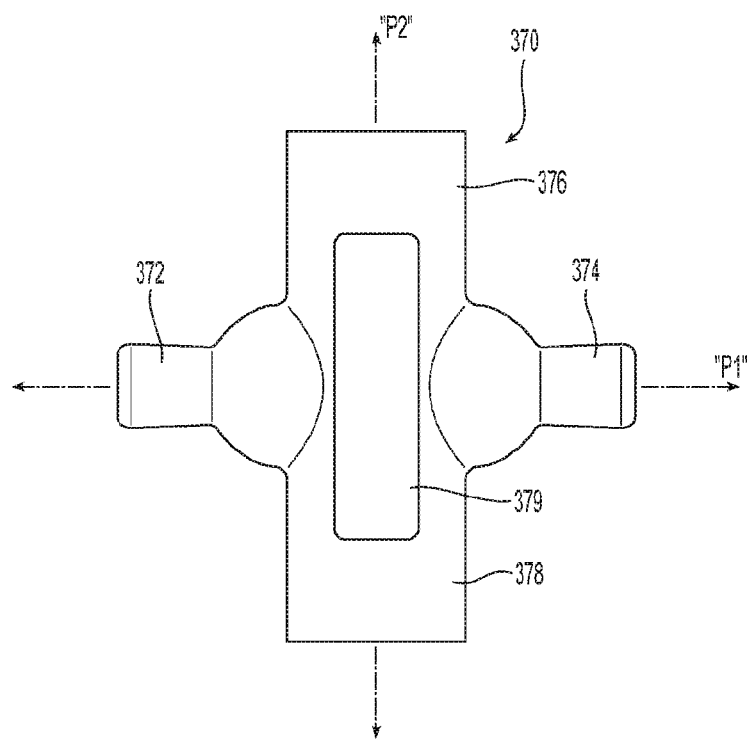
FIG. 27 is a front view of a pivot of the second articulation assembly of FIGS. 25 and 26.

More specifically, and with particular reference to FIGS. 26 and 27, first jaw 310 includes an aperture 312 adjacent its proximal end, which is configured to rotatably or pivotally engage a first, lateral pivot pin 372 of pivot 370. Second jaw 320 includes an aperture 322 adjacent its proximal end, which is configured to rotatably or pivotally engage a second, lateral pivot pin 374 of pivot 370. This mechanical engagement between first jaw 310 and pivot 370, and second jaw 320 and pivot 370 enable jaws 310, 320 to pivot between an open position (FIGS. 31-33) and an approximated position (FIGS. 34-42).

With continued reference to FIGS. 26 and 27, pivot 370 also includes an upper pivot portion 376 and a lower pivot portion 378. Upper pivot portion 376 rotatably engages an upper aperture 332 disposed adjacent a distal end of outer tube 330, and lower pivot portion 378 rotatably engages a lower aperture 334 defined adjacent a distal end of outer tube 330. This engagement between pivot 370 and outer tube 330 enables an end effector including first jaw 310 and second jaw 320 to be pivotable about second pivot axis "P2" in the general directions of arrows "F" and "G" in FIG. 25.

Figure 28:
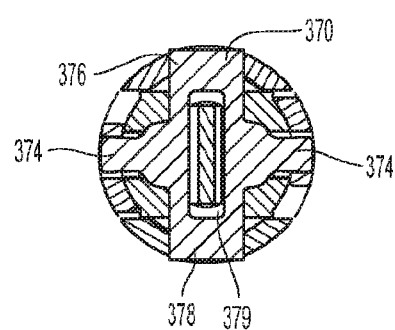
FIG. 28 is a cross-sectional view of a portion of the second articulation assembly of FIGS. 25 and 26.

As shown in FIGS. 27 and 28, pivot 370 also includes an aperture 379 defined longitudinally therethrough. Aperture 379 is rectangular and is configured to allow a portion of drive member 350 to translate therethrough. More particularly, a reduced-perimeter portion 352 of drive member 350 is configured to translate through aperture 379 of pivot 370 to approximate first jaw 310 and second jaw 320, for example. Further, reduced-perimeter portion 352 of drive member 350 is flexible enough to bend or curve laterally in response to articulation of pivoting of the end effector about second pivot axis "P2."

Figure 29:
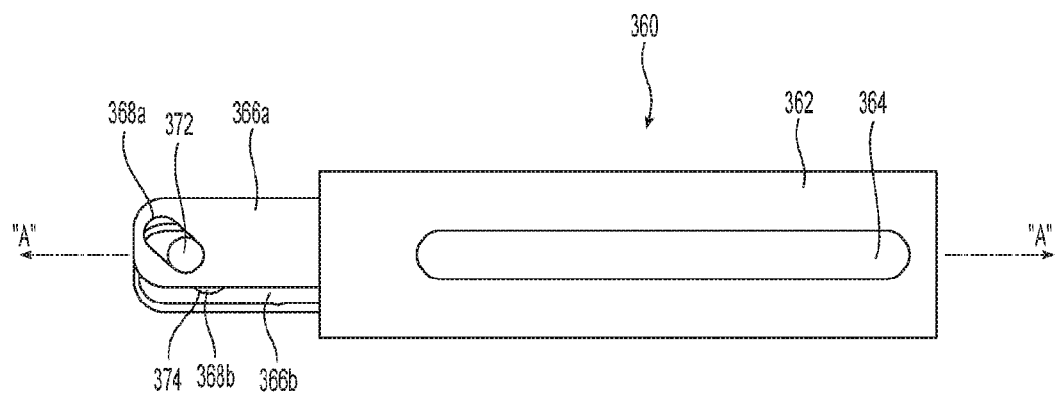
FIG. 29 is a side view of a distal member of the second articulation assembly of FIGS. 25 and 26.
Figure 30:
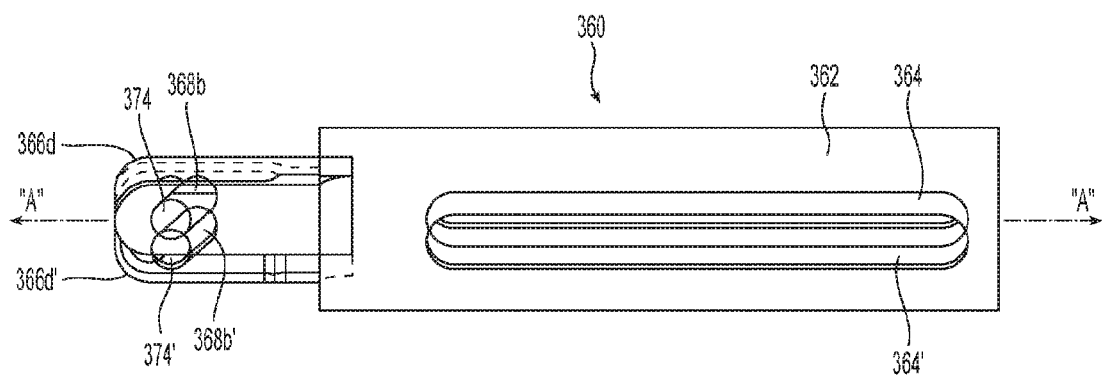
FIG. 30 is a side view of the distal member of FIG. 29 depicting two rotational positions.
Figure 31:
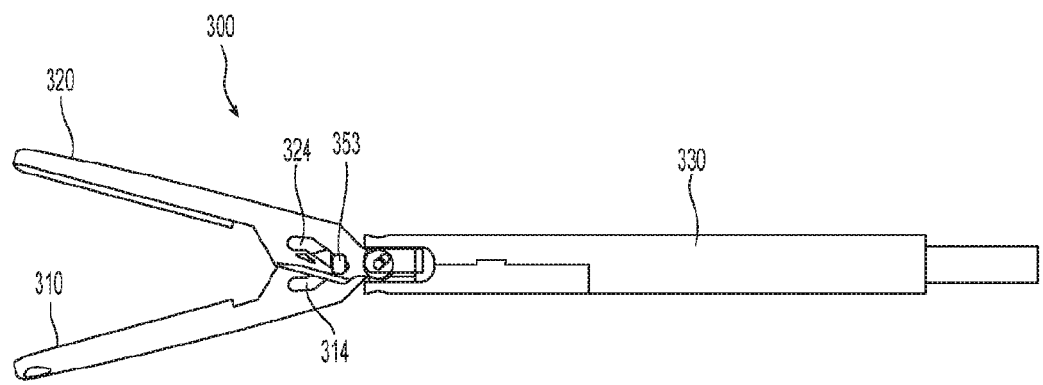
FIGS. 31-33 are side views the second articulation assembly of FIGS. 25 and 26 showing the jaw members in an open position and with various portions omitted.
Figure 32:
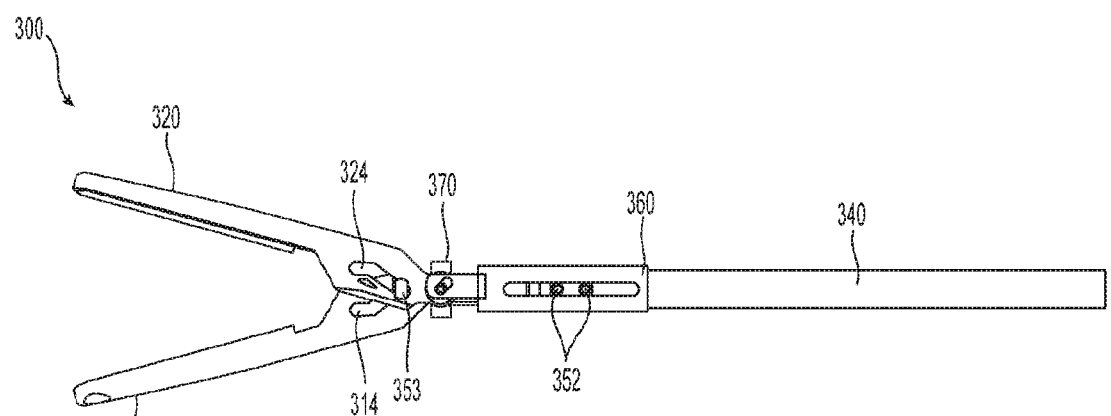
Figure 33:
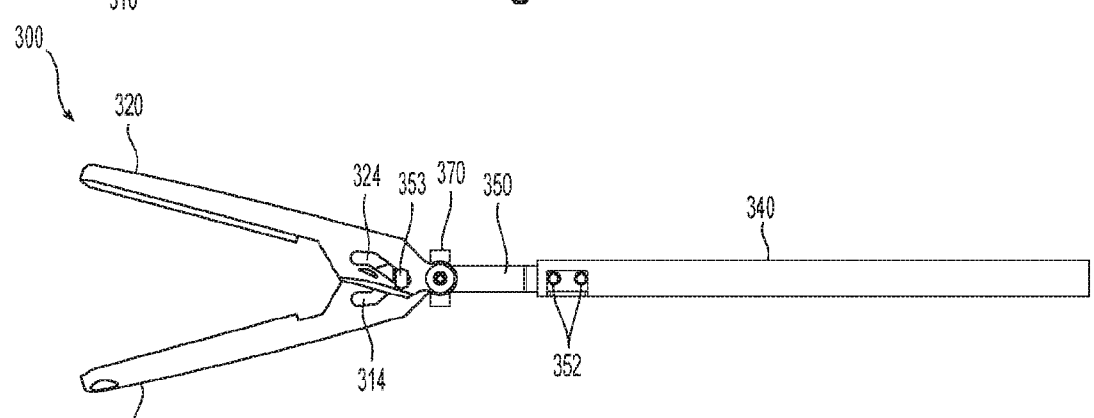
Figure 34:
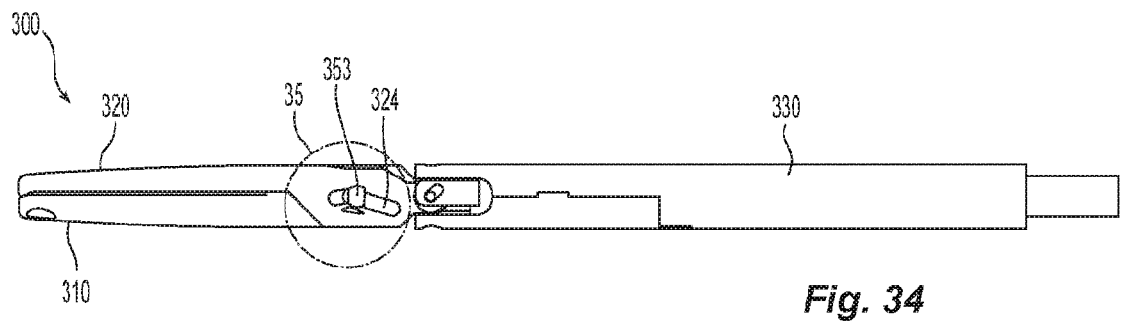
FIG. 34 is a side view of the second articulation assembly of FIGS. 25 and 26 showing the jaw members in an approximated position and with various portions omitted.

Referring now to FIGS. 26 and 29-30, distal member 360 includes a proximal body portion 362 including a pair of longitudinal slots 364 (FIG. 30) extending therethrough (only a single longitudinal slot 364 is visible in FIGS. 26 and 29-30). Distal member 360 also includes a pair of arms 366a, 366b extending distally from body portion 362, and each arm 366a, 366b includes an angled slot 368a, 368b, respectively, extending therethrough. Distal member 360 radially surrounds a proximal portion 354 of drive member 350. Pins 352 extend through each longitudinal slot 364, and, as discussed above, each pin 352 engages hole 351 of drive member 350. Accordingly, drive member 350 is longitudinally translatable with respect to distal member 360.

Additionally, angled slot 368a is configured to engage first, lateral pivot pin 372 of pivot 370, and angled slot 368b is configured to engage second, lateral pivot pin 374 of pivot 370, such first jaw 310 and second jaw 320 are pivotal with respect to distal member 360. Moreover, the fact that angled slots 368a, 368b are angled with respect to the longitudinal axis "A-A" allows first jaw 310 and second jaw 320 to articulate in the directions of "F" and "G" with respect to distal member 360. Additionally, as shown in FIGS. 29 and 30, first arm 366a is vertically offset from the longitudinal axis "A-A" with respect to second arm 366b.

Accordingly, longitudinal translation or rotation of distal member 360 causes lateral pivot pins 372 and 374 to rotate about the second pivot axis "P2," which causes articulation of first jaw 310 and second jaw 320 in the general directions of "F" and "G." More particularly, for example, distal translation of distal member 360 with respect to inner tube 340 causes rotation of distal member 360 in a first direction (e.g., clockwise) and causes first jaw 310 and second jaw 320 to articulate in the general direction of arrow "G." Likewise, for instance, proximal translation of distal member 360 with respect to inner tube 340 causes rotation of distal member 360 in a second direction (e.g., counter-clockwise) and causes first jaw 310 and second jaw 320 to articulate in the general direction of arrow "F." For example, FIG. 30 illustrates distal member 360 in two stages of rotation; features shown in the first stage of rotation are indicated by their reference number, and features shown in the second stage of rotation include a prime indication following their reference number.

Figure 43:
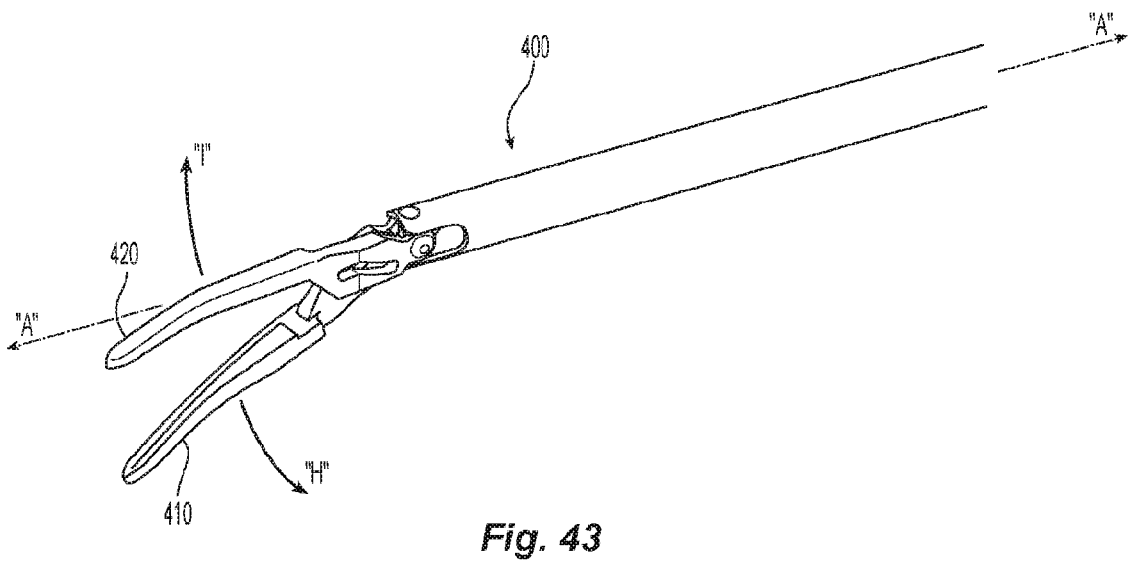
FIG. 43 is a perspective view of a third articulation assembly according to an embodiment of the present disclosure.
Figure 44:
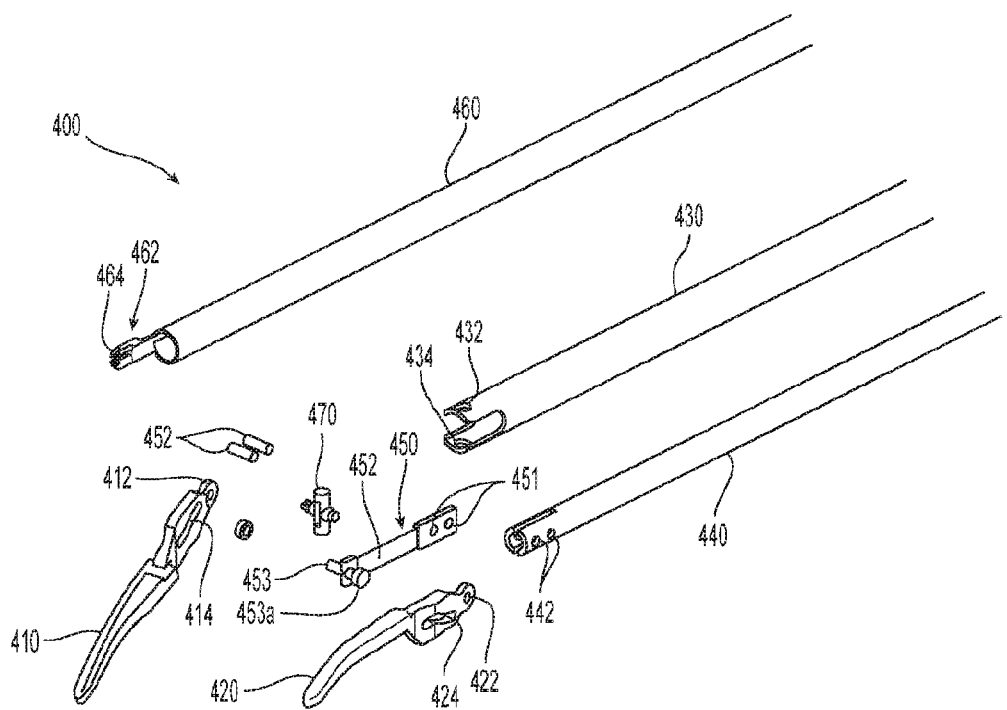
FIG. 44 is an assembly view of the third articulation assembly of FIG. 43.

Referring now to FIGS. 43-47, third articulation mechanism 400 is shown. With particular reference to FIG. 44, third articulation mechanism 400 includes a first jaw 410, a second jaw 420, an outer tube 430, an inner tube 440, a drive member 450, a control member 460, and a pivot 470. Generally, inner tube 440 and drive member 450 are translatable to seal and cut tissue between first jaw 410 and second jaw 420, as described in detail in the patents incorporated hereinabove, and control member 460 is translatable to cause first jaw member 410 and second jaw member 420 to articulate with respect to the longitudinal axis "A-A."

Initially, to seal tissue, a user causes inner tube 440 to be distally translated (e.g., by actuating a lever, knob or button on handle assembly). Inner tube 440 is connected to drive member 450 via pins 452, such that longitudinal translation of inner tube 440 causes a corresponding longitudinal translation of drive member 450. More particularly, pins 452 extend between a pair of apertures 442 adjacent a distal portion of inner tube 440, and a pair of holes 451 defined adjacent a proximal portion of drive member 450.

A drive pin 453 extends through a hole 453a in a distal portion of drive member 450, and extends through a slot 414 of first jaw 410 and a slot 424 of second jaw 420. Longitudinal translation of drive member 450 causes drive pin 453 to travel through slots 414, 424 in a manner similar to the translation of drive member 350 through slots 314, 324 of second articulation assembly 300, discussed above.

With general regard to the pivotal movement of the jaw members, first jaw 410 and second jaw 420 are pivotable about first pivot axis "P1" between an open position and an approximated position, and are pivotable about second pivot axis "P2" in the general directions of arrows "H" and "I" in FIG. 43, which provides a varying degree of articulation.

Figure 45:
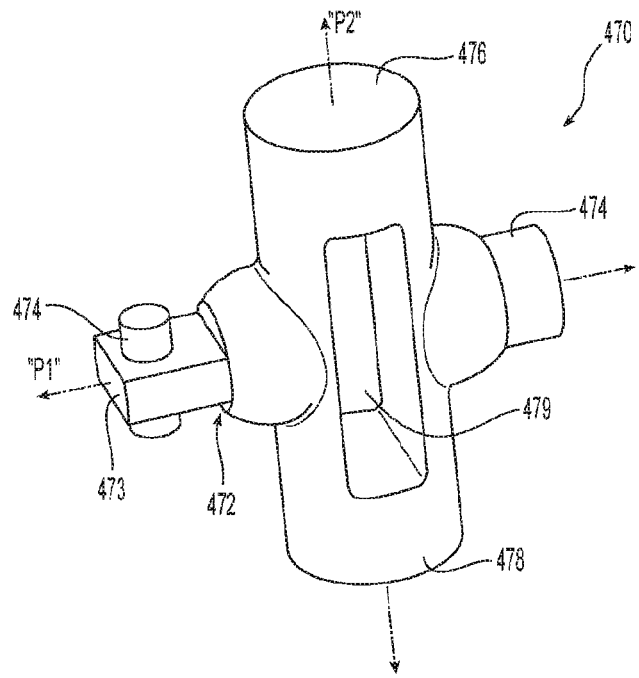
FIG. 45 is a perspective view of a pivot of the third articulation assembly of FIGS. 43 and 44.

More specifically, and with particular reference to FIGS. 43-45, first jaw 410 includes an aperture 412 adjacent its proximal end, which is configured to rotatably or pivotally engage a first, lateral pivot pin 472 of pivot 470. Second jaw 420 includes an aperture 422 adjacent its proximal end, which is configured to rotatably or pivotally engage a second, lateral pivot pin 474 of pivot 470. This mechanical engagement between first jaw 410 and pivot 470, and second jaw 420 and pivot 470 enable jaws 410, 420 to pivot between an open position and an approximated position.

With continued reference to FIGS. 44-45, pivot 470 also includes an upper pivot portion 476 and a lower pivot portion 478. Upper pivot portion 476 rotatably engages an upper aperture 432 disposed adjacent a distal end of outer tube 430, and lower pivot portion 478 rotatably engages a lower aperture 434 disposed adjacent a distal end of outer tube 430. This engagement between pivot 470 and outer tube 430 enables an end effector including first jaw 410 and second jaw 420 to be pivotable about second pivot axis "P2" in the general directions of arrows "H" and "I" in FIG. 43.

Figure 47:
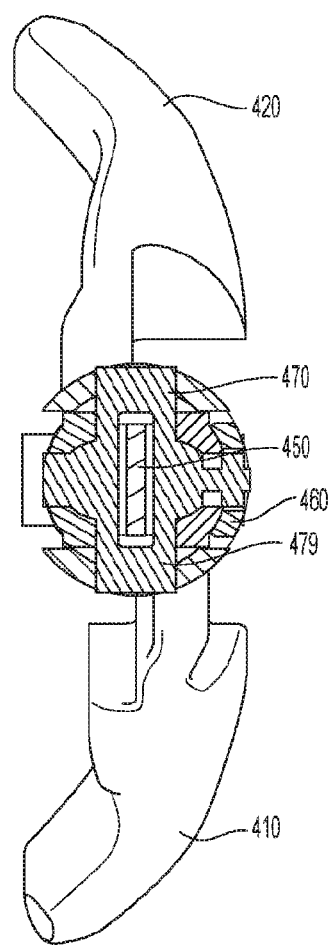
FIG. 47 is a cross-sectional, cut-away view of a portion of the third articulation assembly of FIGS. 43 and 44.

As shown in FIGS. 45 and 47, pivot 470 also includes an aperture 479 extending longitudinally therethrough. Aperture 479 is rectangular and is configured to allow a portion of drive member 450 to translate therethrough. More particularly, a reduced-perimeter portion 452 of drive member 450 is configured to translate through aperture 479 of pivot 470 to approximate first jaw 410 and second jaw 420, for example. Further, reduced-perimeter portion 452 of drive member 450 is flexible enough to bend or curve laterally in response to articulation of pivoting of the end effector about second pivot axis "P2."

Figure 46:
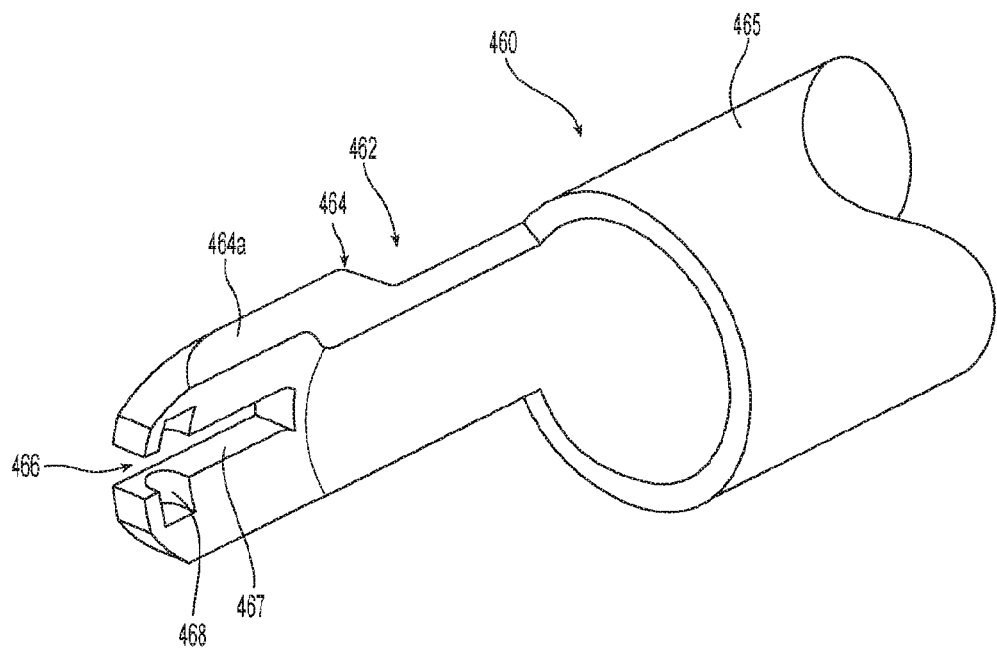
FIG. 46 is a perspective view of a distal portion of a control member of the third articulation assembly of FIGS. 43 and 44.

Referring now to FIGS. 44, 46 and 47, control member 460 extends distally from handle assembly 112 (FIG. 1) and is disposed radially within outer tube 430 along at least a majority of its length. A distal portion 462 of control member 460 includes an arm 464. With particular reference to FIG. 46, a distal portion 464*a* of arm 464 extends radially outward from a main body portion 465 of control member 460. Additionally, arm 464 includes a slot 466 defined therein and configured to engage first, lateral pivot pin 472 of pivot 470. More particularly, slot 466 is configured to engage a first portion 473 of first, lateral pivot pin 472, and a second portion 474 of first, lateral pivot pin 472. Second portion 474 extends perpendicularly from first portion 473 (see FIG. 45), thus forming a T-shaped portion. Correspondingly, slot 466 of control member 460 includes a first portion 467 configured to engage first portion 473 of first, lateral pivot pin 472, and includes a second portion 468 configured to engage second portion 474 of first, lateral pivot pin 472. Second portion 468 of slot 466 extends perpendicularly from first portion 467 of slot 466, and is thus T-shaped.

Accordingly, longitudinal translation of control member 460 causes pivot 470 to rotate about second pivot axis "P2," which results in articulation of jaw members 410, 420. More particularly, for example, movement of control member 460 in a first longitudinal direction (e.g., distally) causes control member 460 to push first, lateral pivot pin 472 distally, which causes pivot 470 to rotate in a first direction, and which causes first jaw 410 and second jaw 420 to articulate in the general direction of arrow "H." Likewise, for instance, proximal movement of control member 460 causes control member 460 to pull first, lateral pivot pin 472 proximally, which causes pivot 470 to rotate in a second direction, and which causes first jaw 410 and second jaw 420 to articulate in the general direction of arrow "I."

The various embodiments disclosed herein may also be configured to work with robotic surgical systems and what is commonly referred to as "Telesurgery." Such systems employ various robotic elements to assist the surgeon and allow remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of surgeons or nurses may prepare the patient for surgery and configure the robotic surgical system with one or more of the surgical instruments disclosed herein while another surgeon (or group of surgeons) remotely controls the instrument(s) via the robotic surgical system. As can be appreciated, a highly skilled surgeon may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the surgeon to produce a corresponding movement of the working ends of any type of surgical instrument (e.g., end effectors, graspers, knifes, scissors, etc.) which may complement the use of one or more of the embodiments described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

The master handles may include various sensors to provide feedback to the surgeon relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions.

Figure 48:
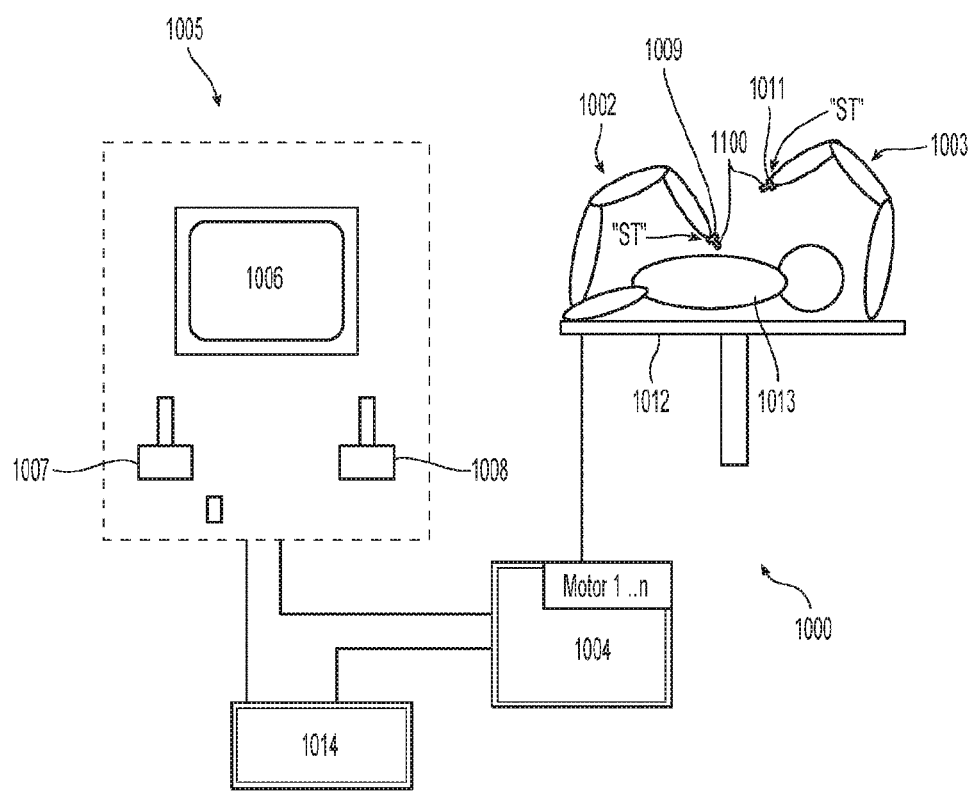
FIG. 48 is a schematic illustration of a surgical system in accordance with the present disclosure.

With particular reference to FIG. 48, a medical work station is shown generally as work station 1000 and generally may include a plurality of robot arms 1002, 1003; a control device 1004; and an operating console 1005 coupled with control device 1004. Operating console 1005 may include a display device 1006, which may be set up in particular to display three-dimensional images; and manual input devices 1007, 1008, by means of which a person (not shown), for example a surgeon, may be able to telemanipulate robot arms 1002, 1003 in a first operating mode.

Each of the robot arms 1002, 1003 may include a plurality of members, which are connected through joints, and an attaching device 1009, 1011, to which may be attached, for example, a surgical tool "ST" supporting an end effector 1100, in accordance with any one of several embodiments disclosed herein, as will be described in greater detail below.

Robot arms 1002, 1003 may be driven by electric drives (not shown) that are connected to control device 1004. Control device 1004 (e.g., a computer) may be set up to activate the drives, in particular by means of a computer program, in such a way that robot arms 1002, 1003, their attaching devices 1009, 1011 and thus surgical tool "ST" (including end effector 1100) execute a desired movement according to a movement defined by means of manual input devices 1007, 1008. Control device 1004 may also be set up in such a way that it regulates the movement of robot arms 1002, 1003 and/or of the drives.

Medical work station 1000 may be configured for use on a patient 1013 lying on a patient table 1012 to be treated in a minimally invasive manner by means of end effector 1100. Medical work station 1000 may also include more than two robot arms 1002, 1003, the additional robot arms likewise being connected to control device 1004 and being telemanipulatable by means of operating console 1005. A medical instrument or surgical tool (including an end effector 1100) may also be attached to the additional robot arm. Medical work station 1000 may include a database 1014, in particular coupled to with control device 1004, in which are stored, for example, pre-operative data from patient/living being 1013 and/or anatomical atlases.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An articulation assembly for use with a surgical instrument including an elongated portion, a first jaw member and a second jaw member, the articulation assembly comprising:
    a plurality of joints, each joint defining:
        a plurality of openings extending longitudinally therethrough;
        a central opening extending longitudinally therethrough;
        a pair of projections extending from a first surface; and
        a pair of grooves extending at least partially through a second surface, each groove of at least one joint configured to engage one projection of the pair of projections from an adjacent joint;
    a plurality of cables, each cable extending through one opening of the plurality of openings of each joint;
    a first drive member extending through the central opening of each joint; and
    a second drive member extending through the central opening of each joint, wherein each of the first drive member and the second drive member includes a semi-circular cross-section at locations that are longitudinally aligned with each joint.

2. The articulation assembly according to claim 1, wherein each projection of at least one joint is configured to be at least partially positioned within one groove of the pair of grooves of an adjacent joint.

3. The articulation assembly according to claim 1, wherein each projection of at least one joint includes an arcuate surface configured to contact an arcuate wall defining one groove of the pair of grooves of an adjacent joint.

4. The articulation assembly according to claim 1, wherein each joint of the plurality of joints is substantially identical.

5. The articulation assembly according to claim 1, wherein each joint of the plurality of joints includes a pair of contours and a pair of platforms, each contour of the pair of contours of at least one joint is configured to engage one platform of the pair of platforms of an adjacent joint.

6. The articulation assembly according to claim 5, wherein each contour of the pair of contours of at least one joint is configured to pivot with respect to one platform of the pair of platforms of an adjacent joint.

7. The articulation assembly according to claim 6, wherein each contour of the pair of contours of at least one joint is configured to pivot against a flat surface of one platform of the pair of platforms of an adjacent joint.

8. The articulation assembly according to claim 5, wherein each projection of each joint is 90° offset from each contour of the pair of contours.

9. The articulation assembly according to claim 1, further comprising a cable actuator disposed in mechanical cooperation with a handle assembly of the surgical instrument, the cable actuator including at least one aperture, the plurality of cables extending through the at least one aperture of the actuator.

10. The articulation assembly according to claim 1, wherein the plurality of cables includes four cables.

11. The articulation assembly according to claim 10, further comprising a cable actuator disposed in mechanical cooperation with a handle assembly of the surgical instrument, the cable actuator including a first aperture and a second aperture defined therethrough, two cables of the plurality of cables extending through the first aperture of the actuator, and two cables of the plurality of cables extending through the second aperture of the actuator.

12. An articulation assembly for use with a surgical instrument including an elongated portion, a first jaw member and a second jaw member, the articulation assembly comprising:
    a plurality of joints, each joint defining:
        a plurality of openings extending longitudinally therethrough;
        a central opening extending longitudinally therethrough;
        a pair of projections extending from a first surface; and
        a pair of grooves extending at least partially through a second surface, each groove of at least one joint configured to engage one projection of the pair of projections from an adjacent joint;
    a plurality of cables, each cable extending through one opening of the plurality of openings of each joint; and
    a first drive member extending through the central opening of each joint, wherein each joint of the plurality of joints includes a pair of contours and a pair of platforms, each contour of the pair of contours of at least one joint is configured to engage one platform of the pair of platforms of an adjacent joint, wherein each projection of each joint is 90° offset from each contour of the pair of contours.

13. An articulation assembly for use with a surgical instrument including an elongated portion, a first jaw member and a second jaw member, the articulation assembly comprising:
    a plurality of joints, each joint defining:
        a plurality of openings extending longitudinally therethrough;
        a central opening extending longitudinally therethrough;
        a pair of projections extending from a first surface; and
        a pair of grooves extending at least partially through a second surface, each groove of at least one joint configured to engage one projection of the pair of projections from an adjacent joint;
    a plurality of cables, each cable extending through one opening of the plurality of openings of each joint;

a first drive member extending through the central opening of each joint, wherein the plurality of cables includes four cables; and a cable actuator disposed in mechanical cooperation with a handle assembly of the surgical instrument, the cable actuator including a first aperture and a second aperture defined therethrough, two cables of the plurality of cables extending through the first aperture of the actuator, and two cables of the plurality of cables extending through the second aperture of the actuator.

* * * * *